(12) United States Patent
Bacon et al.

(10) Patent No.: US 8,192,369 B2
(45) Date of Patent: Jun. 5, 2012

(54) APPARATUS FOR COCKING A BIOPSY DEVICE

(75) Inventors: Chad J. Bacon, Coopersville, MI (US); Stephen F. Peters, Hickory Corners, MI (US)

(73) Assignee: Inrad, Inc., Grand Rapids, MI (US)

( * ) Notice: Subject to any disclaimer, the term of this patent is extended or adjusted under 35 U.S.C. 154(b) by 399 days.

(21) Appl. No.: 12/474,489

(22) Filed: May 29, 2009

(65) Prior Publication Data

US 2009/0299221 A1   Dec. 3, 2009

Related U.S. Application Data

(60) Provisional application No. 61/057,370, filed on May 30, 2008.

(51) Int. Cl.
*A61B 10/00* (2006.01)

(52) U.S. Cl. ........ 600/567; 600/562; 600/564; 606/167; 606/185; 606/186

(58) Field of Classification Search .......... 600/562–568; 606/167, 170–172
See application file for complete search history.

(56) References Cited

U.S. PATENT DOCUMENTS

| | | | |
|---|---|---|---|
| 5,036,860 A | 8/1991 | Leigh et al. | |
| 5,392,790 A | 2/1995 | Kanner et al. | |
| 5,951,489 A * | 9/1999 | Bauer | 600/567 |
| 6,083,176 A | 7/2000 | Terwilliger | |
| 6,106,484 A | 8/2000 | Terwilliger | |
| 6,283,925 B1 | 9/2001 | Terwilliger | |
| 7,008,382 B2 | 3/2006 | Adams et al. | |
| 2006/0155210 A1 | 7/2006 | Beckman et al. | |

* cited by examiner

*Primary Examiner* — Max Hindenburg
*Assistant Examiner* — Megan Leedy
(74) *Attorney, Agent, or Firm* — McGarry Bair PC

(57) ABSTRACT

A biopsy device includes a housing, a stylet carriage having a strike, a cannula carriage having a strike, and a cocking element comprising a catch carried by a resilient shaft that extends along an operational axis of the biopsy device. To arm the biopsy device, the cocking element is moved in a first arming stroke such that the catch engages the strike on the cannula carriage to deflect the resilient shaft from the operational axis such that the catch clears the strike on the stylet.

21 Claims, 22 Drawing Sheets

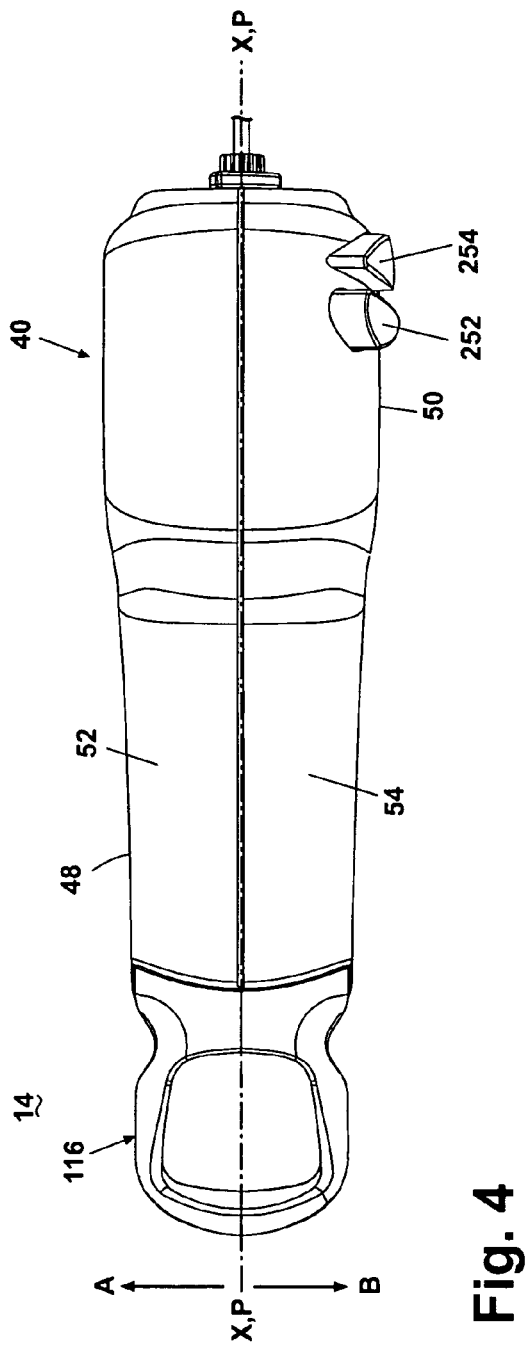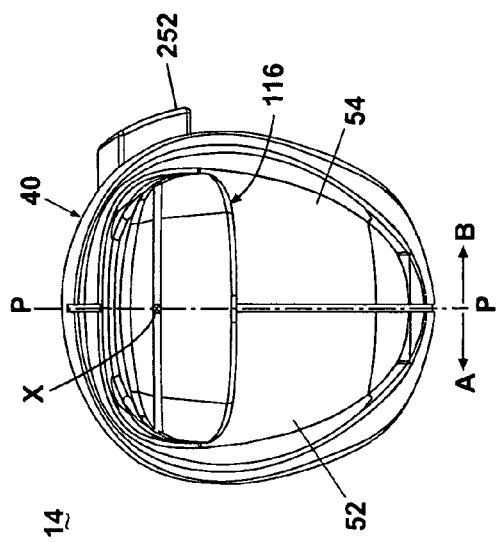
Fig. 4
Fig. 5

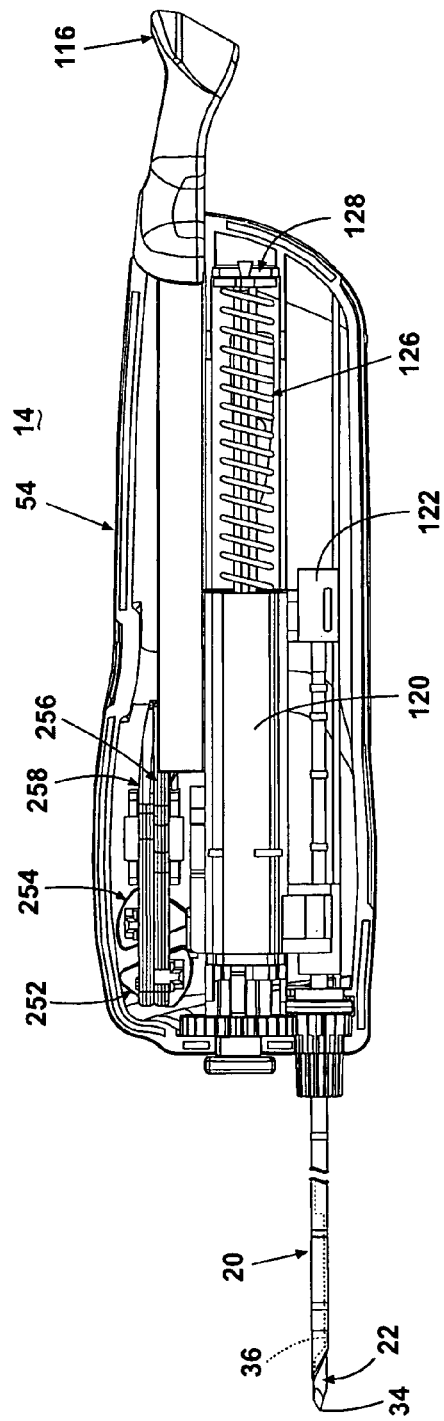
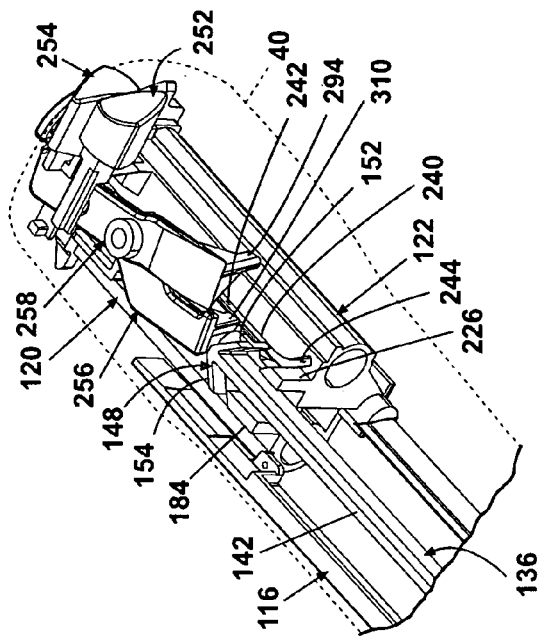
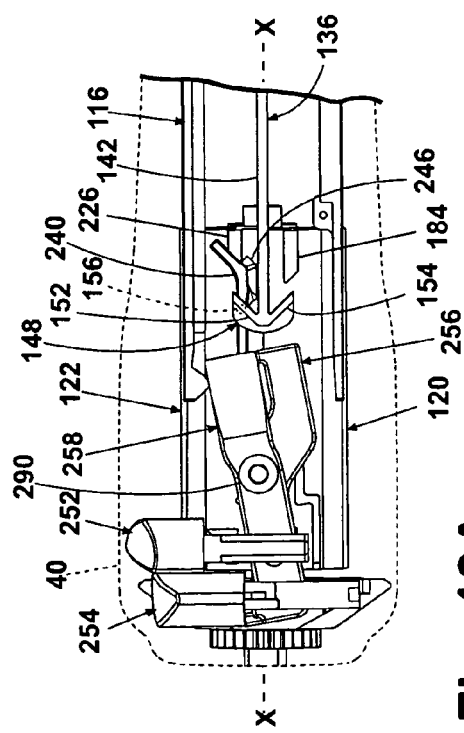
Fig. 12A
Fig. 14A
Fig. 13A

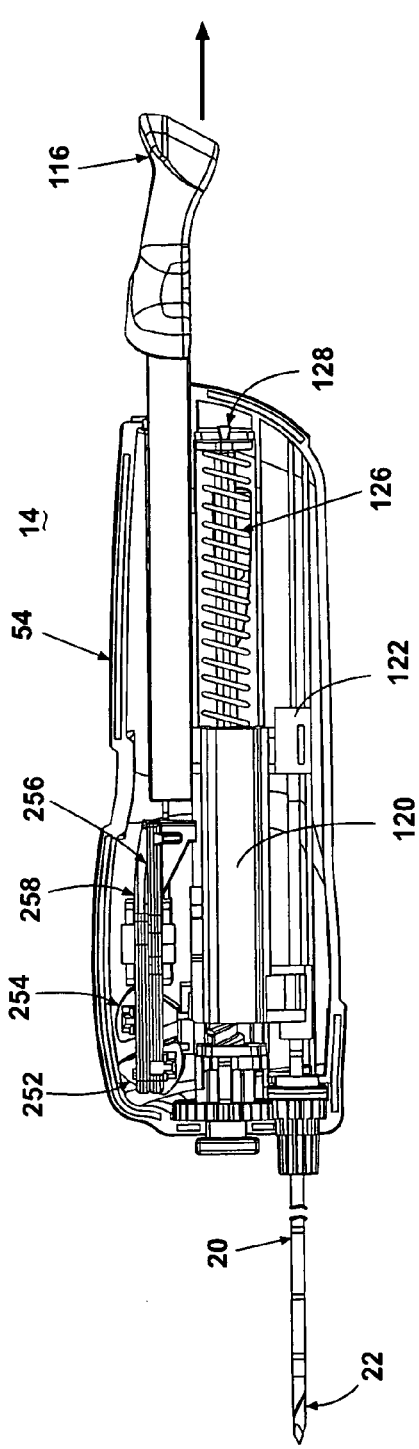
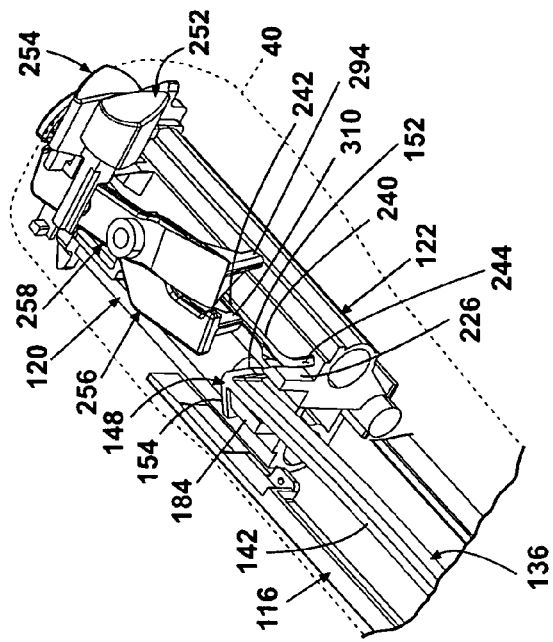
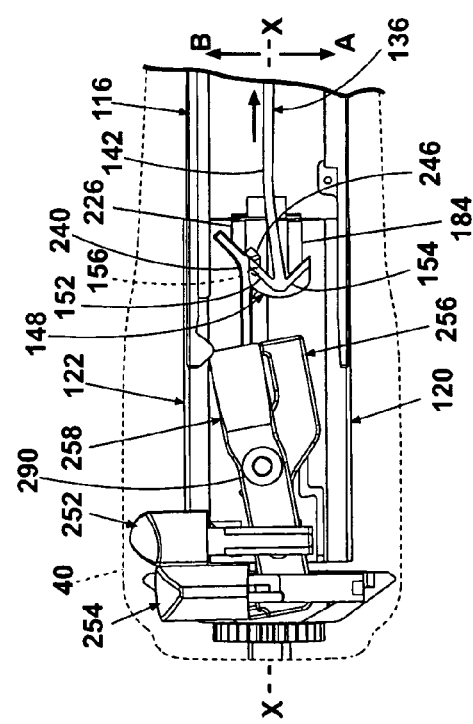

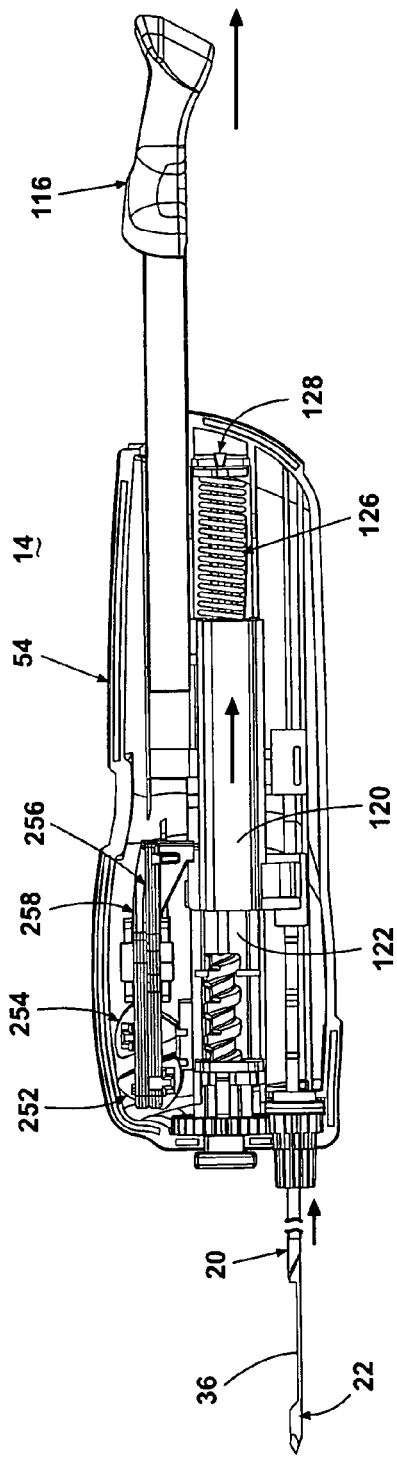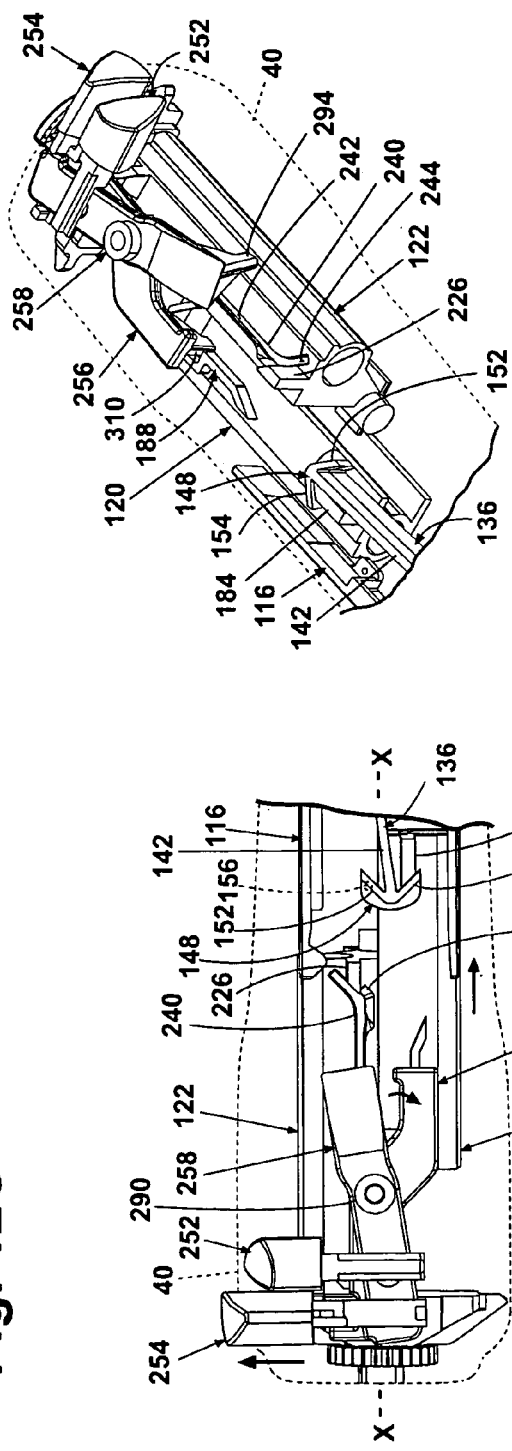

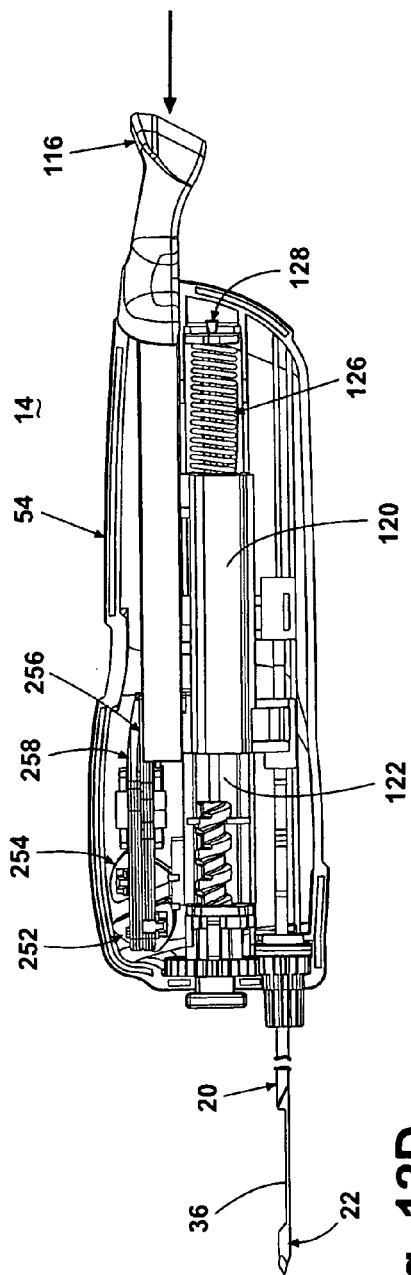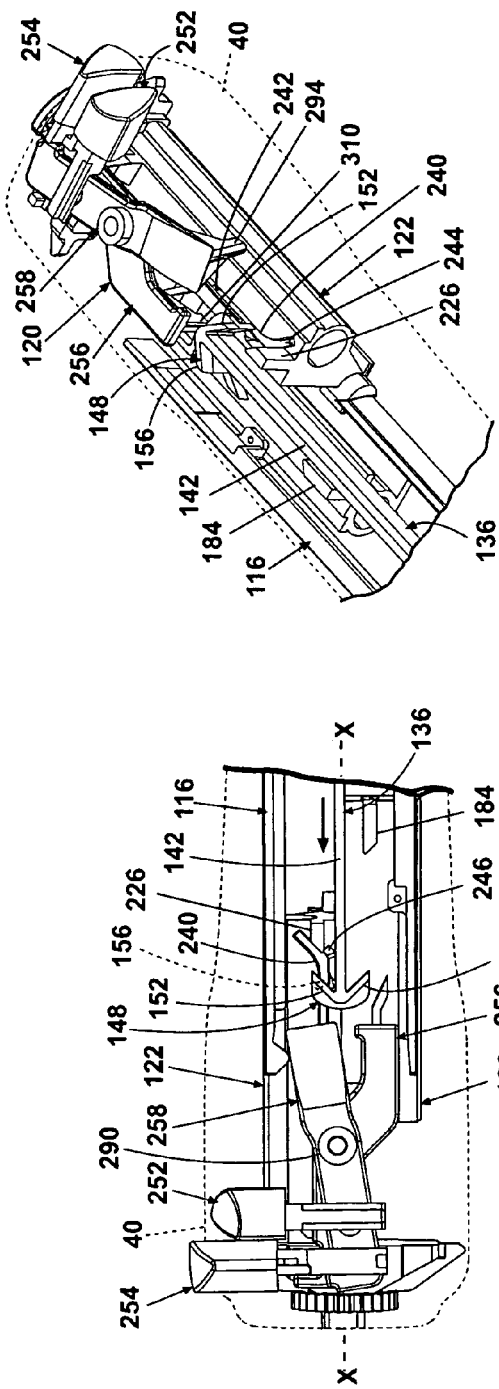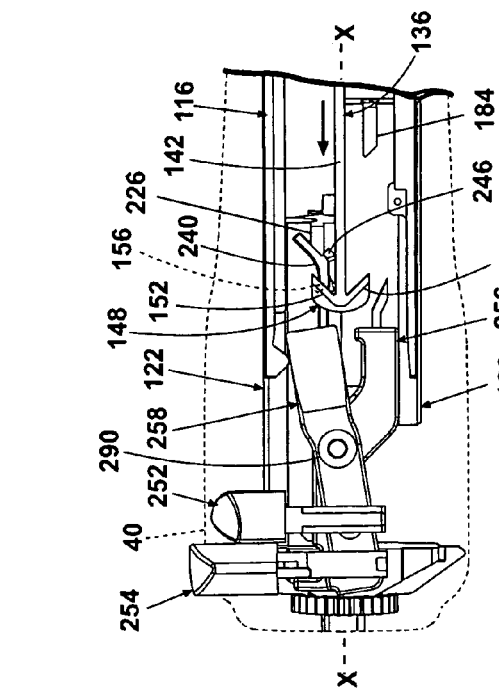

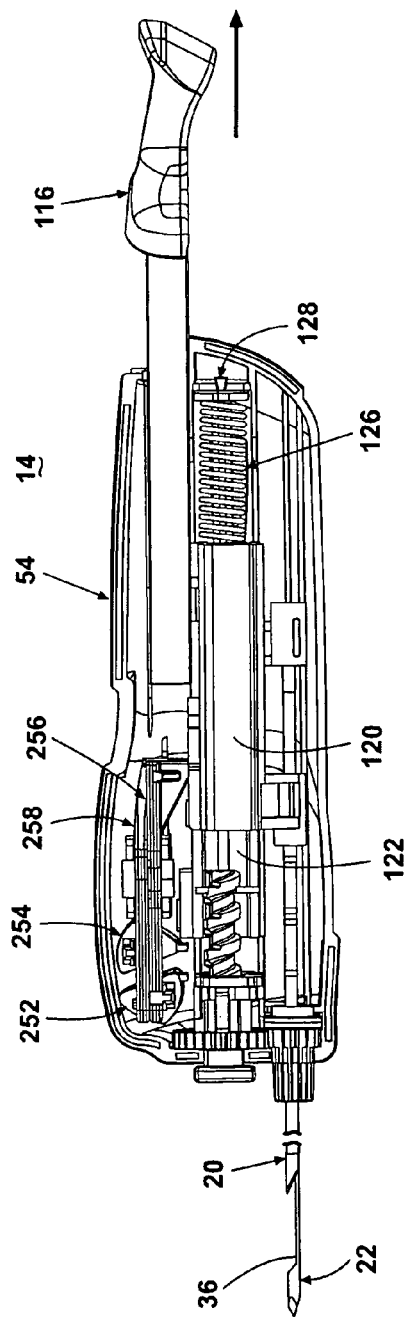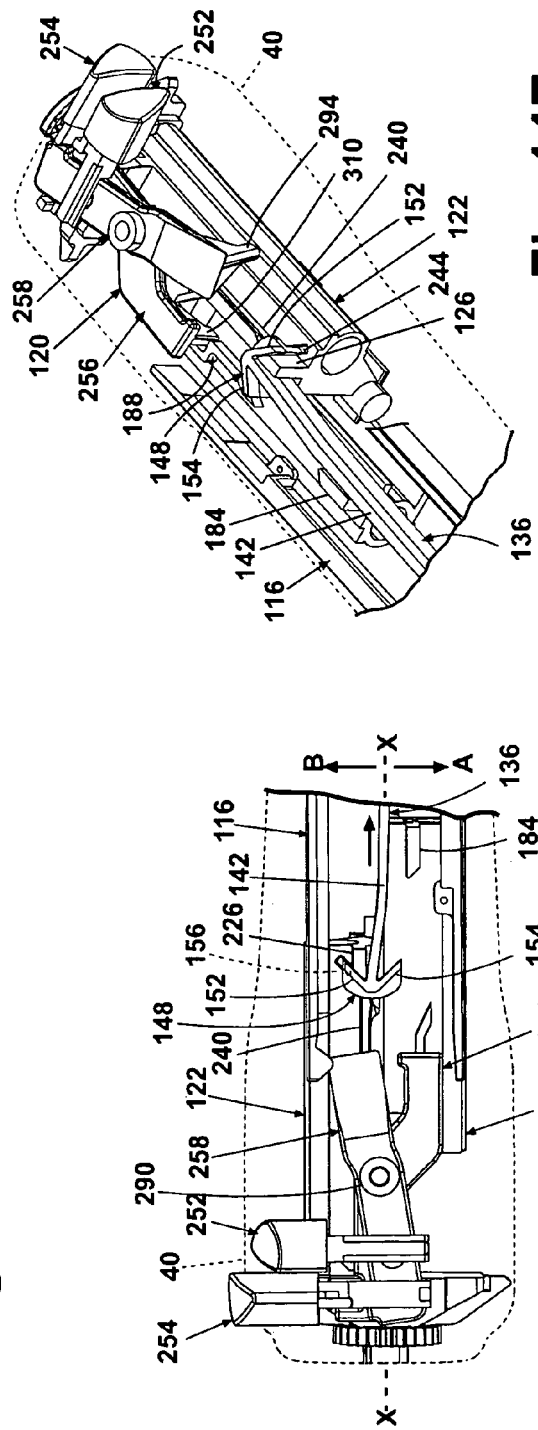

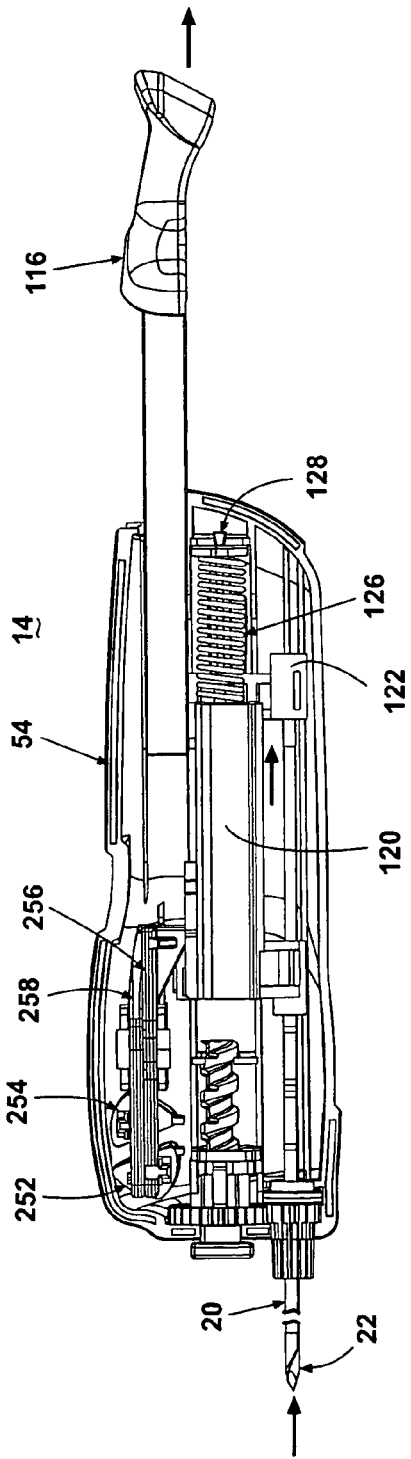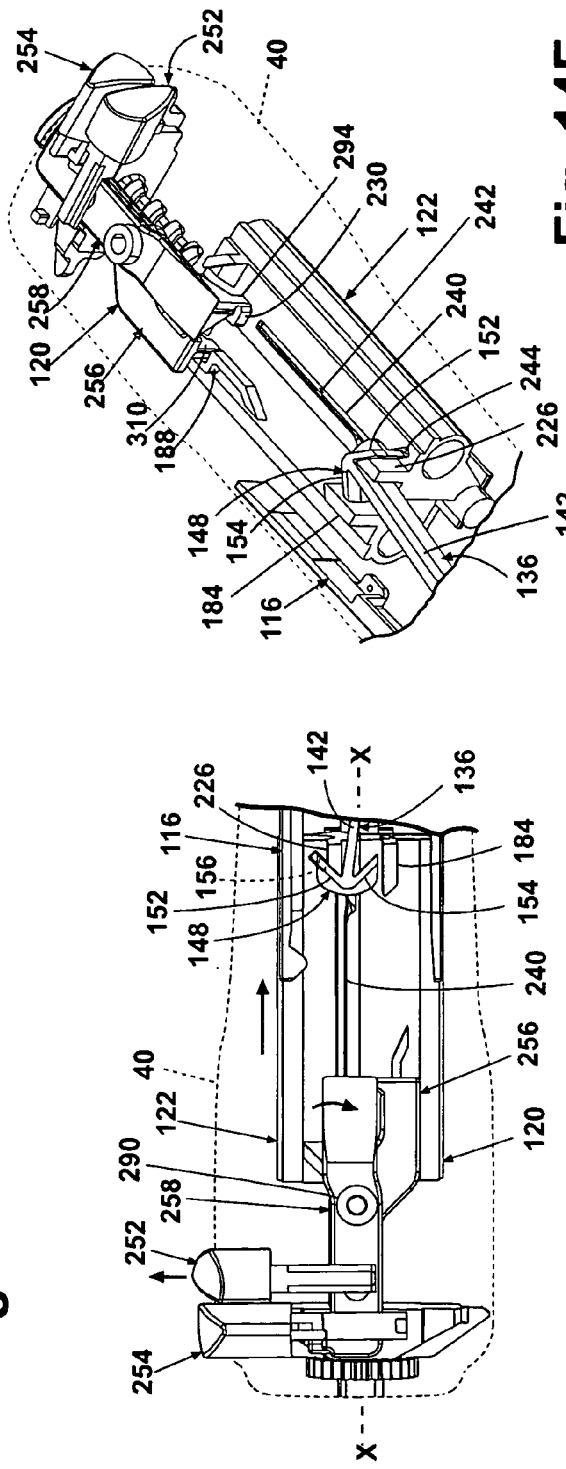

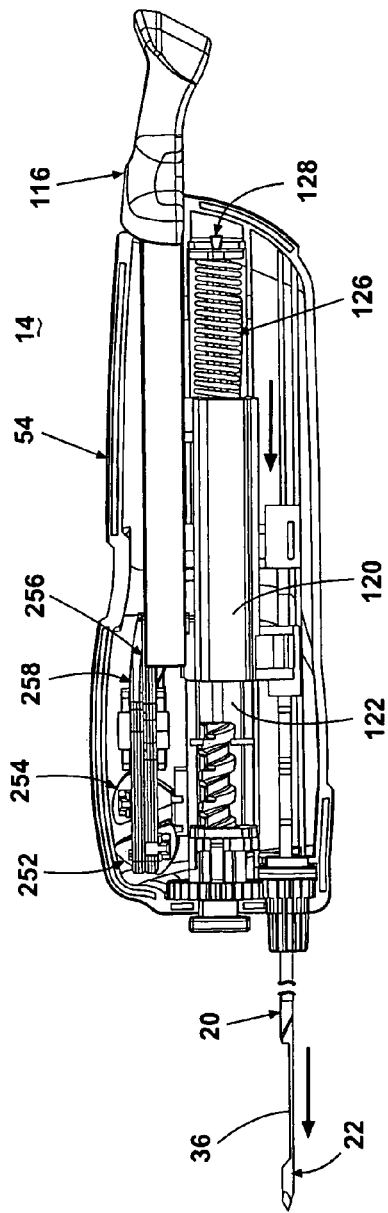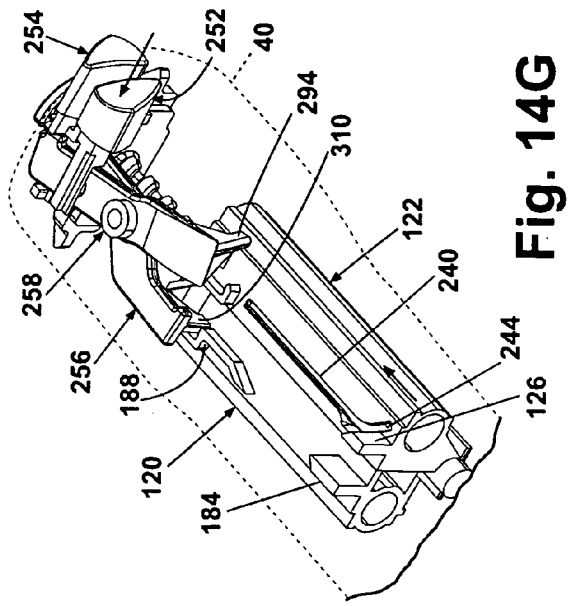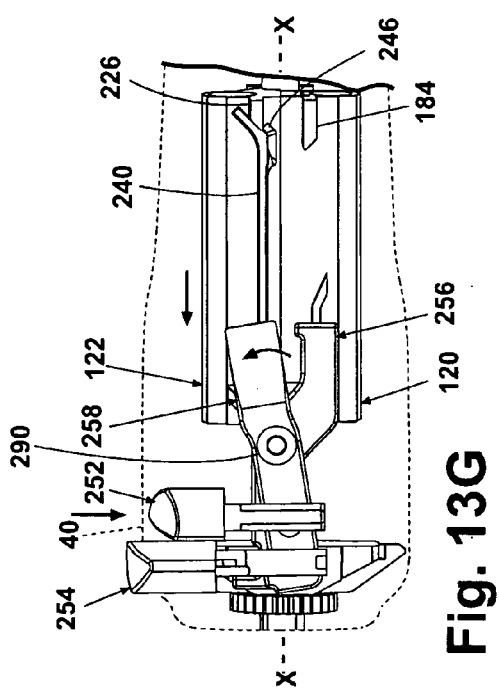

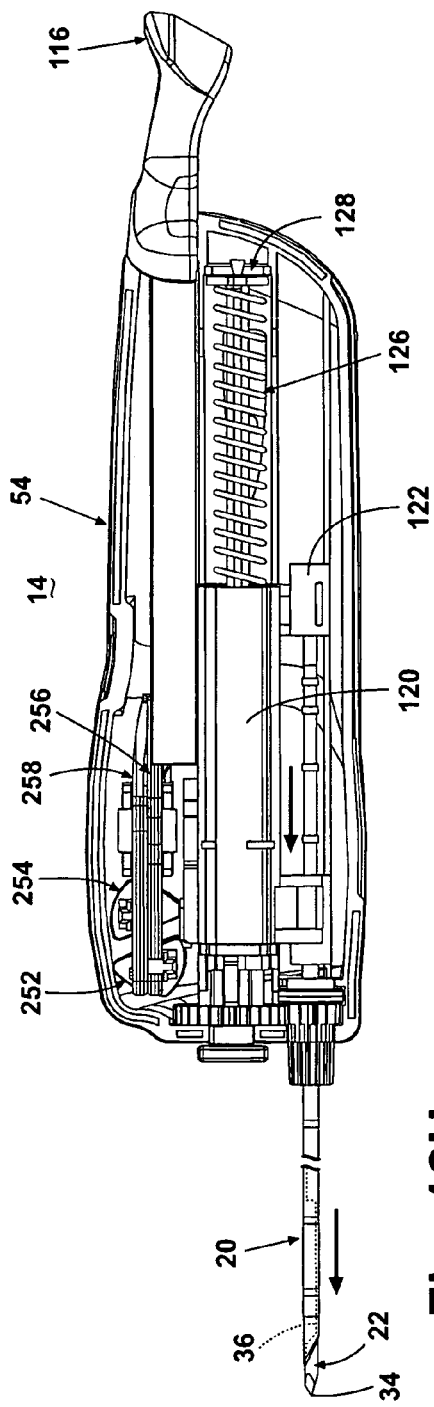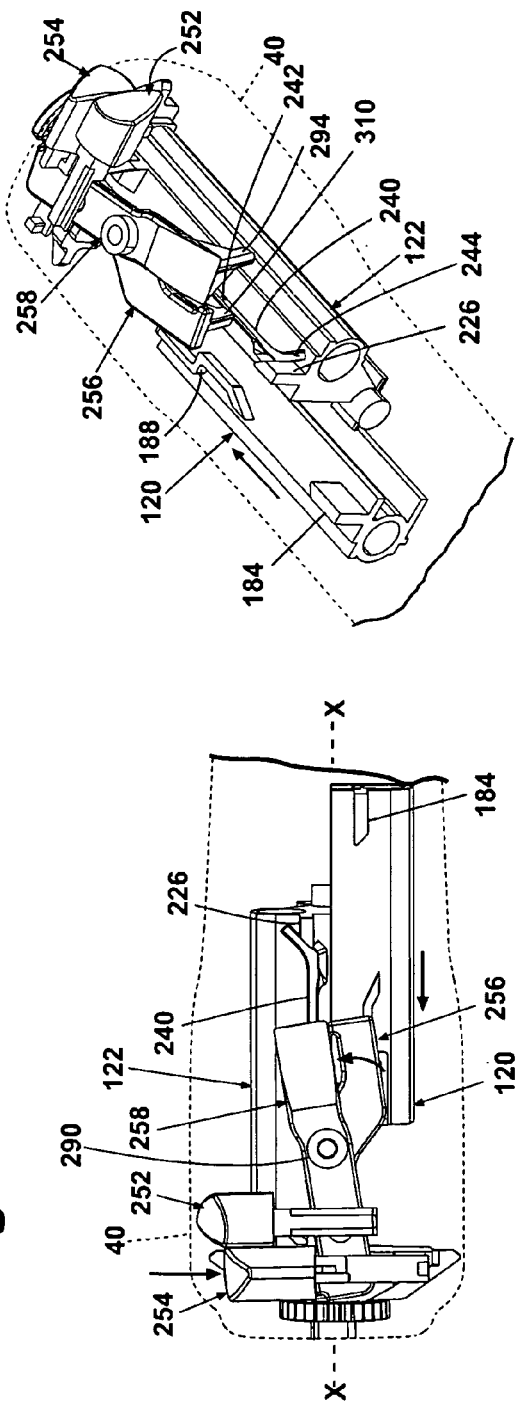

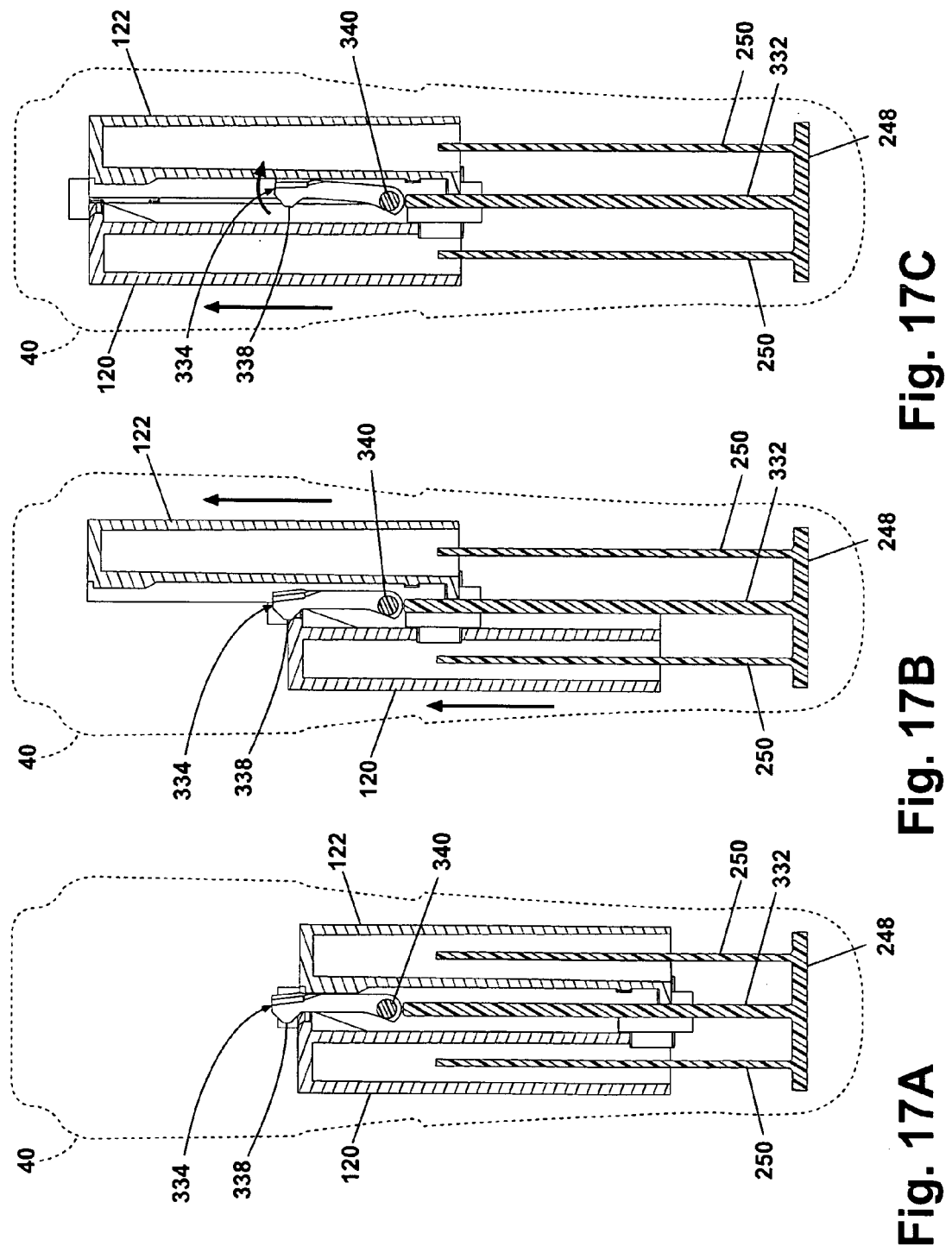

APPARATUS FOR COCKING A BIOPSY DEVICE

CROSS-REFERENCE TO RELATED APPLICATION

This application claims the benefit of U.S. Provisional Patent Application No. 61/057,370, filed May 30, 2008, which is incorporated herein by reference in its entirety.

BACKGROUND OF THE INVENTION

It is frequently necessary to sample or remove a sample from a suspect tissue for testing. In humans, such a sample removal is particularly useful in the diagnosis and treatment of cancerous or pre-cancerous conditions. In the case of suspected cancer, particularly cancer of the breast, early detection and diagnosis is critical to the success of the patient's treatment and recovery.

Various techniques are available to aid in detection and diagnosis, including physical examination and imaging, such as mammography, x-ray, ultrasound, magnetic resonance imaging (MRI), and the like. When a condition is detected that suggests the possibility of cancer, a biopsy can be performed to obtain tissue samples for a complete diagnosis.

One biopsy technique frequently performed utilizes a cannula assembly comprising a stylet and a cannula that telescopically receives the stylet. One group of cannula assemblies is based on the combination of a notched inner stylet and an outer severing cannula. The stylet is retained within the lumen of the outer cannula such that the pointed end of the stylet closes off the open end of the cannula. The stylet and cannula are advanced into the tissue mass until they are near the desired biopsy site. The stylet is then advanced relative to the outer cannula to expose the notch to the biopsy site where the tissue prolapses into the notch. The outer cannula is then advanced to sever the tissue in the notch. Another group of cannula assemblies is based on a coring cannula in combination with a non-notched stylet. The stylet is used to plug the end of the coring cannula during the insertion of the coring cannula into the tissue adjacent the biopsy site. The coring cannula is then advanced relative to the stylet into the biopsy site to retain a sample within the coring cannula.

Many biopsy devices are provided with an actuator assembly for automating the firing of a cannula assembly. The actuator assembly can include springs that bias the cannula and stylet to the fired position. The cannula assembly must be cocked or armed prior to firing, which requires moving the cannula and stylet against the spring force. Some biopsy devices arm the cannula and stylet simultaneously. The disadvantage to this type of cocking operation is that the user must over come the spring force biasing both the cannula and stylet at once. Other biopsy devices arm the cannula and stylet sequentially. The advantage to this type of cocking operation is that biopsy device requires less effort to arm, since the user must only overcome the spring force biasing one of the cannula or the stylet at a time.

SUMMARY OF THE INVENTION

The invention relates to a biopsy device for the percutaneous removal of a specimen from a tissue mass. The biopsy device comprises a housing defining an interior having an operational axis, a cannula carriage provided in the housing for reciprocal movement between an armed position and a fired position within the interior and having a cannula strike laterally offset from the operational axis in a first lateral direction, a stylet carriage provided in the housing for reciprocal movement between an armed position and a fired position within the interior and having a stylet strike laterally offset from the operational axis in a second lateral direction opposite the first lateral direction and proximal of the cannula strike when the cannula carriage and the stylet carriage are in the fired position, and a cocking element slidably mounted to the housing for movement between a first position and a second position to define an arming stroke, and having catch carried by a resilient shaft extending along the operational axis. With the stylet and cannula carriages in the fired positions, upon a first arming stroke, the catch engages the cannula strike to deflect the resilient shaft from the operational axis in the first lateral direction such that the catch clears the stylet strike and the cannula carriage is moved to the armed position.

BRIEF DESCRIPTION OF THE DRAWINGS

In the drawings:

FIG. 4 is a top view of the actuator assembly illustrated in FIG. 1

FIG. 5 is a back view of the actuator assembly illustrated in FIG. 1.

FIGS. 12A-12H are longitudinal sections, FIGS. 13A-13I are top views, and

FIGS. 14A-14I are rear perspective views of the biopsy device from FIG. 1 showing various stages of operation, including:

(A) the biopsy device in the uncocked or fired position;
(B) the deflection of the cocking element during the first arming stroke;
(C) the completion of the first arming stroke;
(D) the return of the cocking element after the first arming stroke;
(E) the deflection of the cocking element during the second arming stroke;
(F) the completion of the second arming stroke;

(G) the first step of firing the biopsy device according to a two-step actuating operation;

(H) the second step of firing the biopsy device according to a two-step actuating operation; and (I) the firing of the biopsy device according to a one-step actuating operation.

Figure 15:
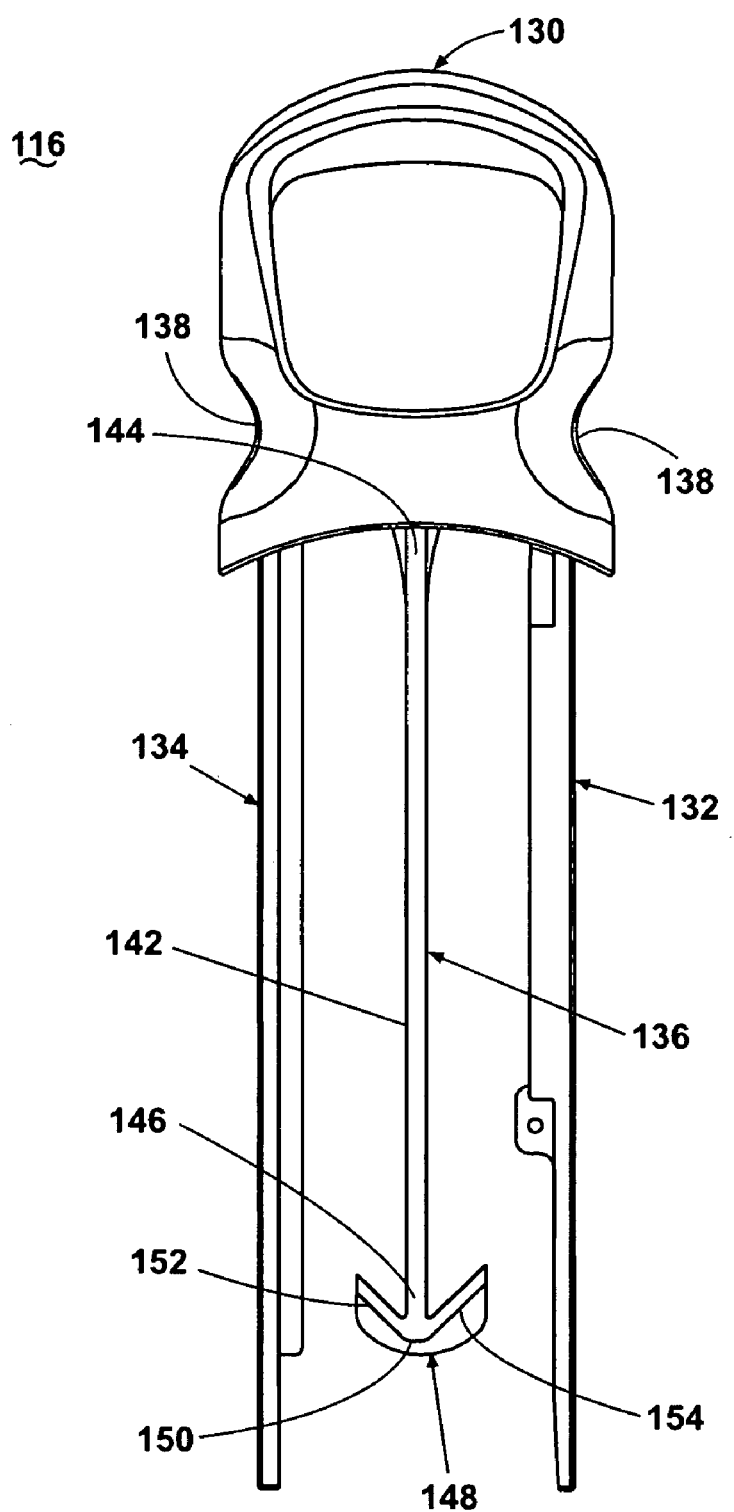

FIG. 15 is a top perspective view of a cocking element according to a second embodiment of the biopsy device according to the invention.

Figure 16A:
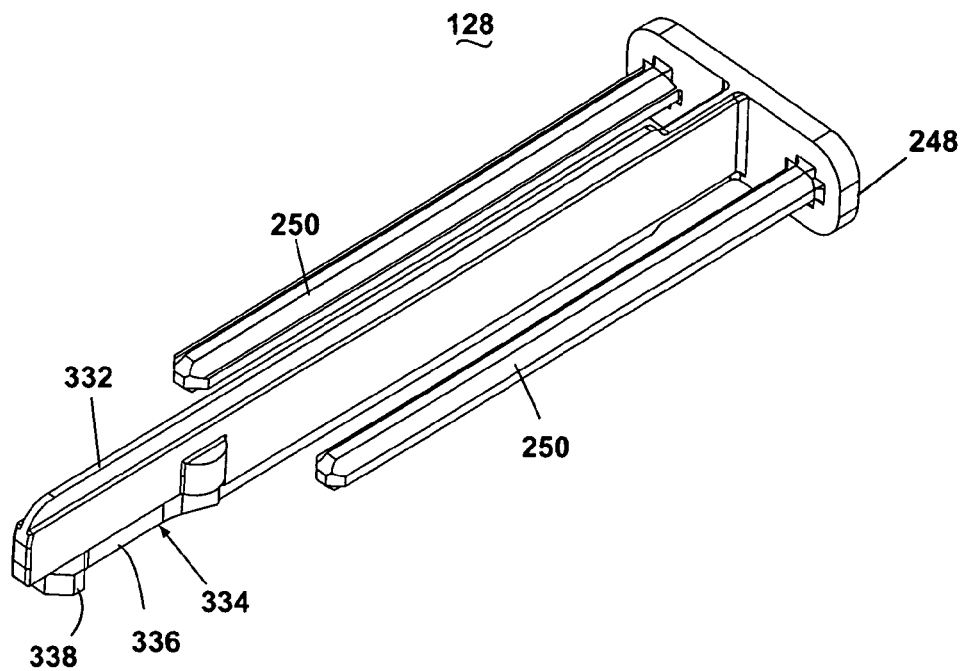

FIG. 16A is a top perspective view of a spring guide having a delay arm according to the second embodiment.

Figure 16B:
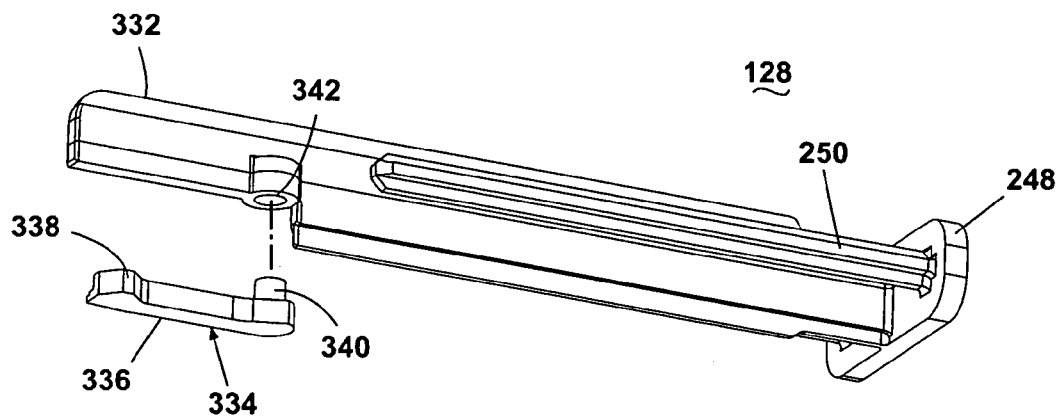

FIG. 16B is an exploded, bottom perspective view of the spring guide and delay arm from FIG. 16A.

FIGS. 17A-C are schematic sectional views taken through the spring guide of FIG. 16A, the cannula carriage, and the stylet carriage, showing the operation of the delay arm during the firing of the biopsy device according to a one-step actuating operation.

DESCRIPTION OF AN EMBODIMENT OF THE INVENTION

Figure 1:
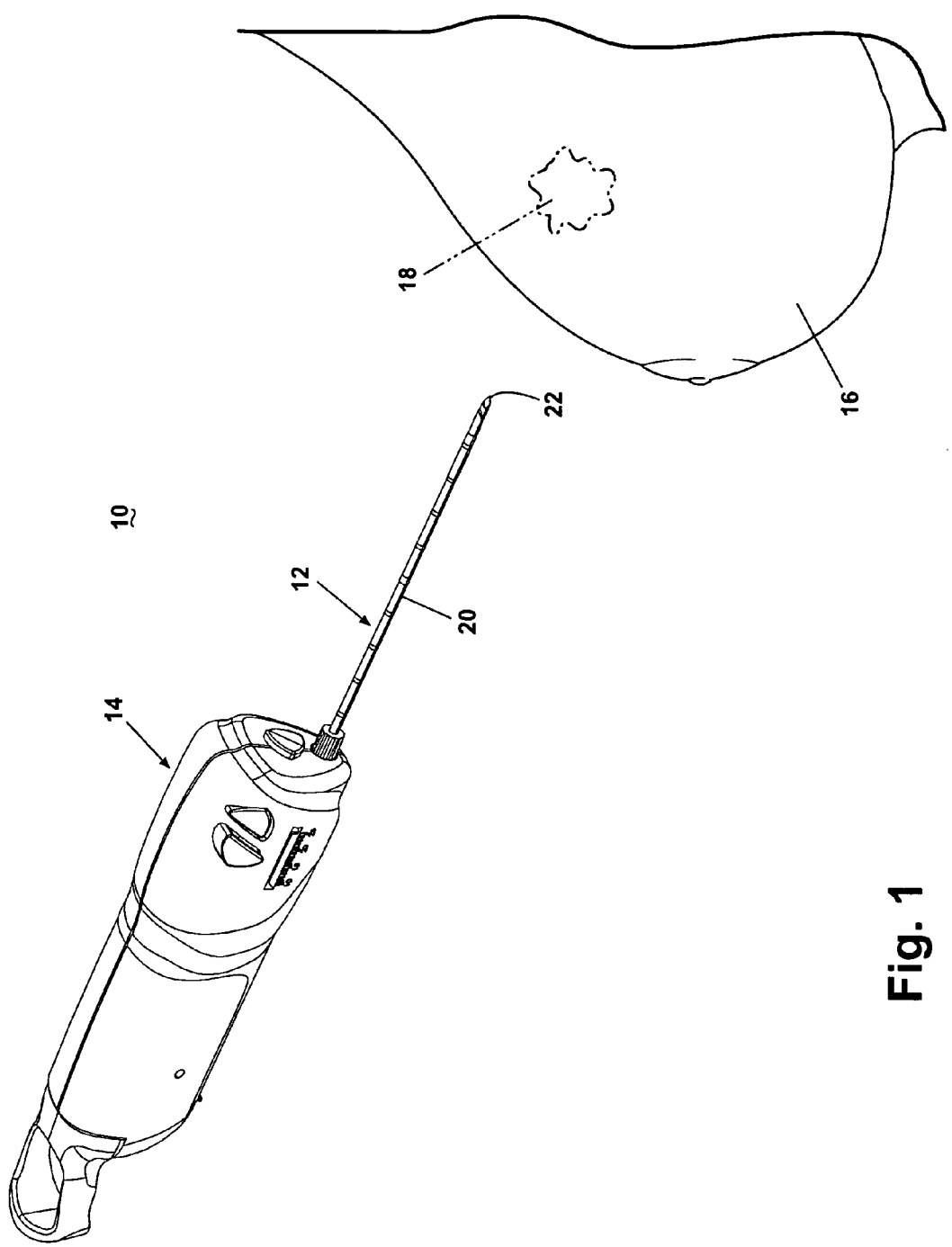
FIG. 1 is a perspective view of a lesion within a tissue mass and a biopsy device comprising a cannula assembly and an actuator assembly according to a first embodiment of the invention for obtaining a biopsy sample from the lesion.

Referring to FIG. 1, a biopsy device 10 according to a first embodiment of the invention is illustrated comprising a cannula assembly 12 structurally and operably connected to an actuator assembly 14. The cannula assembly 12 is utilized to penetrate a tissue mass 16 for obtaining a biopsy sample from a lesion 18. The cannula assembly 12 can comprise a cannula 20 and a stylet 22 in coaxially telescoping relationship. While the cannula assembly 12 is described herein as comprising the cannula 20 and the notched stylet 22 purposes of illustrating the operation of the biopsy device 10, it is understood that other cannula assemblies can be employed with the actuation assembly 14 of the invention. The biopsy device 10 can also optionally be characterized as a "biopsy gun".

As used herein with respect to the biopsy device 10, the terms "distal" or "forward", or any variations thereof, refer to or in a direction toward the end of the cannula assembly 12 and/or the actuator assembly 14 that is directed toward the lesion 18. The terms "proximal" or "rearward", or any variations thereof, refer to or in a direction toward the end of the cannula assembly 12 and/or the actuator assembly 14 that is directed away the lesion 18.

The actuator assembly 14 comprises a hand-held device capable of controlling the acquisition and removal of the biopsy sample, alternately referred to as a biopsy specimen, from the lesion 18 through the cocking and firing of the cannula assembly 12. As illustrated, the cocking is manual and the firing is automated. The actuator assembly 14 is capable of cocking the cannula 20 and stylet 22 independently. The actuator assembly 14 has the additional capability of firing the cannula 20 and stylet 22 with one triggering action, or firing the cannula 20 and stylet 22 independently. The actuator assembly 14 also functions as a handle for the biopsy device 10.

Figure 2:
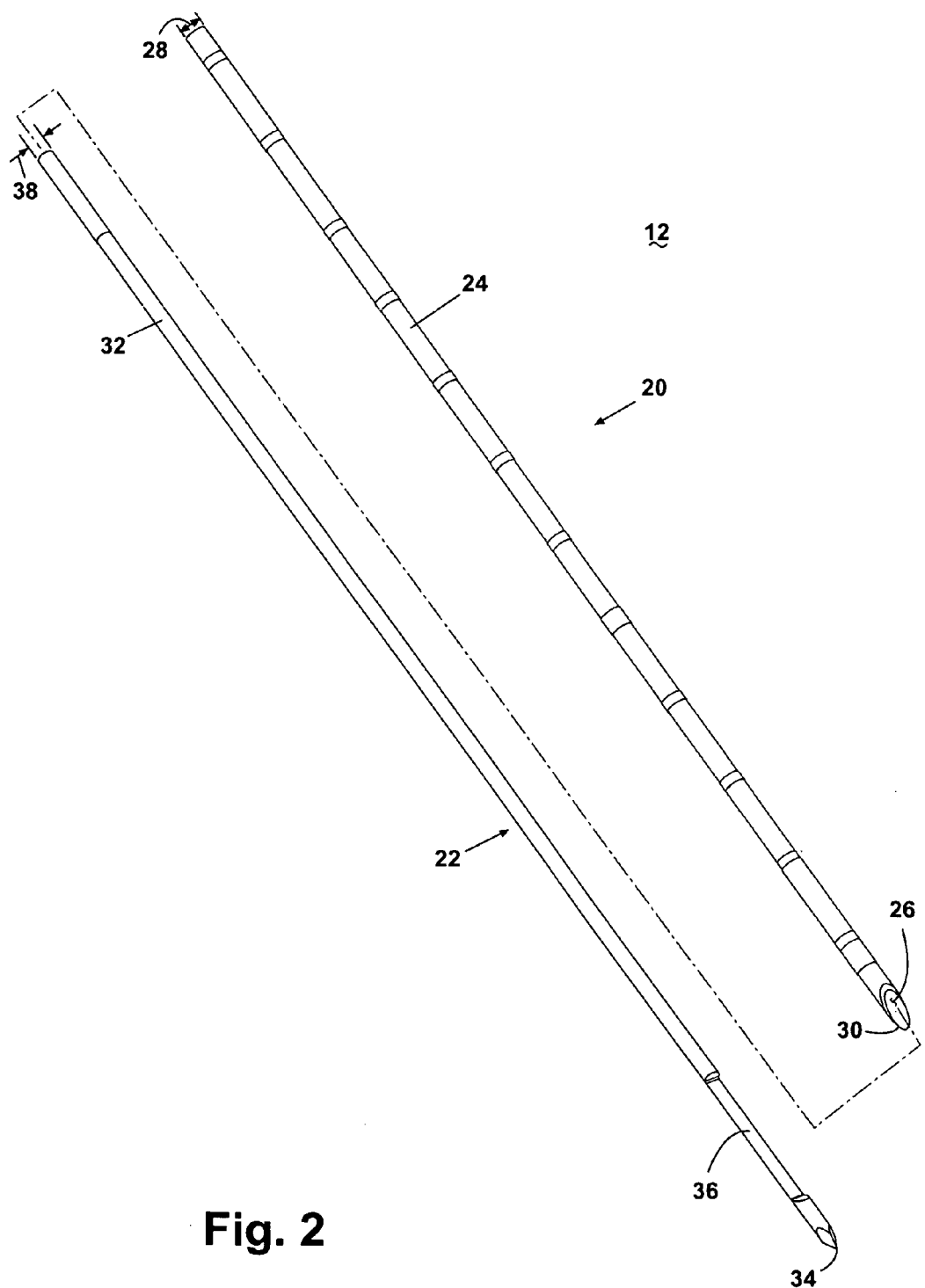
FIG. 2 is an exploded view of the cannula assembly illustrated in FIG. 1, the cannula assembly comprising a cannula and a stylet.

Referring to FIG. 2, the cannula 20 is an elongated, tubular member having an annular wall 24 defining a lumen 26 therethrough having an inner diameter 28. The cannula 20 terminates at a distal end in a cutting edge 30. The stylet 22 is an elongated, usually solid, cylindrical member comprising a stylet body 32 terminating in a pointed distal penetration tip 34. As illustrated, the penetration tip 34 is shown as comprising a trochar point; however, the penetration tip 34 can have other conventional configurations, such as a bevel point. The stylet body 32 can include a notch 36 near the distal penetration tip 34. The stylet body 32 has a constant outer diameter 38 which is somewhat smaller than the inner diameter 28 of the cannula 20 so that the stylet 22 is slidably received within the lumen 26 of the cannula 20.

Figure 3:
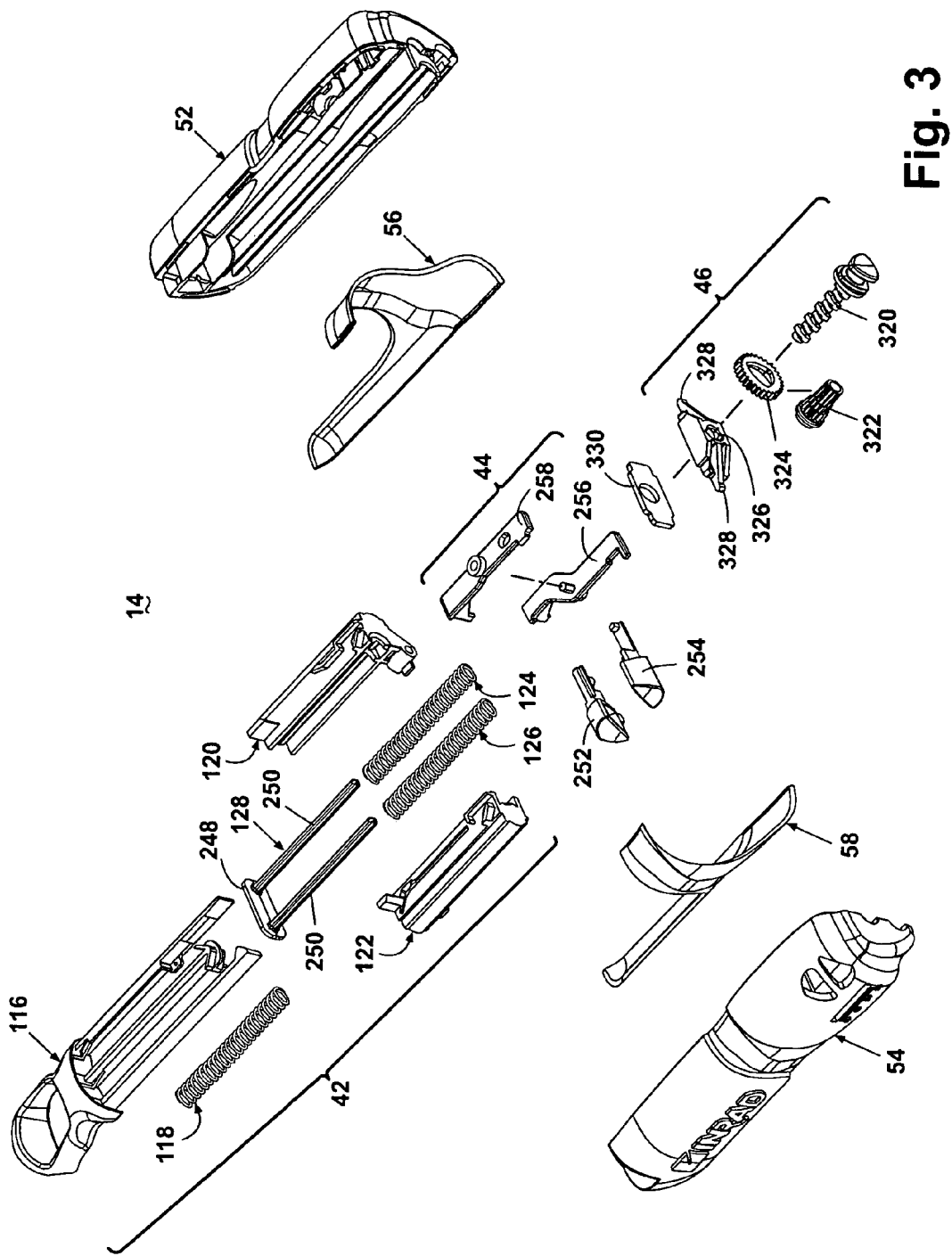
FIG. 3 is an exploded view of the actuator assembly illustrated in FIG. 1, the actuator assembly including a cocking/operation assembly, an actuator assembly and a sample size control assembly.

Referring to FIGS. 3-4, the actuator assembly 14 comprises an outer housing 40 that supports the cannula assembly 12 and both the internal and external components of the actuator assembly 14, including a cocking/operation assembly 42, an actuator assembly 44 and a sample size control assembly 46. The outer housing 40 is shaped to provide a rear grip portion 48 to provide an ergonomic, functional handle for facilitating the insertion of the cannula assembly 12 into the tissue mass 16 and the recovery of a biopsy sample and an enlarged front bearing portion 50 against which the user's hand or fingers can bear to securely grip the actuator assembly 14. The outer housing 40 includes a right housing shell 52 and a left housing shell 54 adapted for cooperative registry. Each housing shell 52, 54 can have a respective overmolded section 56, 58 to provide a soft tough grip on the outer housing 40. As illustrated herein, the overmolded sections 56, 58 can be shaped to encircle the portion of the outer housing 40 where the user is likely to place their thumb and extend along the bottom side of the outer housing 40 where the user is likely to place their fingers or the palm of their hand.

Referring to FIGS. 4-5, the outer housing 40 can comprise an operational axis X. The operational axis X can be located on an operational plane P extending through the outer housing 40. The operational plane P can be oriented vertically and can be located along the centerline of the biopsy device, therefore locating the operational axis X along the centerline of the biopsy device. The operational axis X can extend generally horizonally along the operational plane P.

While the operational axis X is illustrated extending along the centerline of the biopsy device 10, it may be off the centerline depending on the configuration of the biopsy device 10. Similarly, the operation plane P may also be an orientation other than vertically. It may be horizontal or somewhere between vertical and horizontal.

Figure 6:
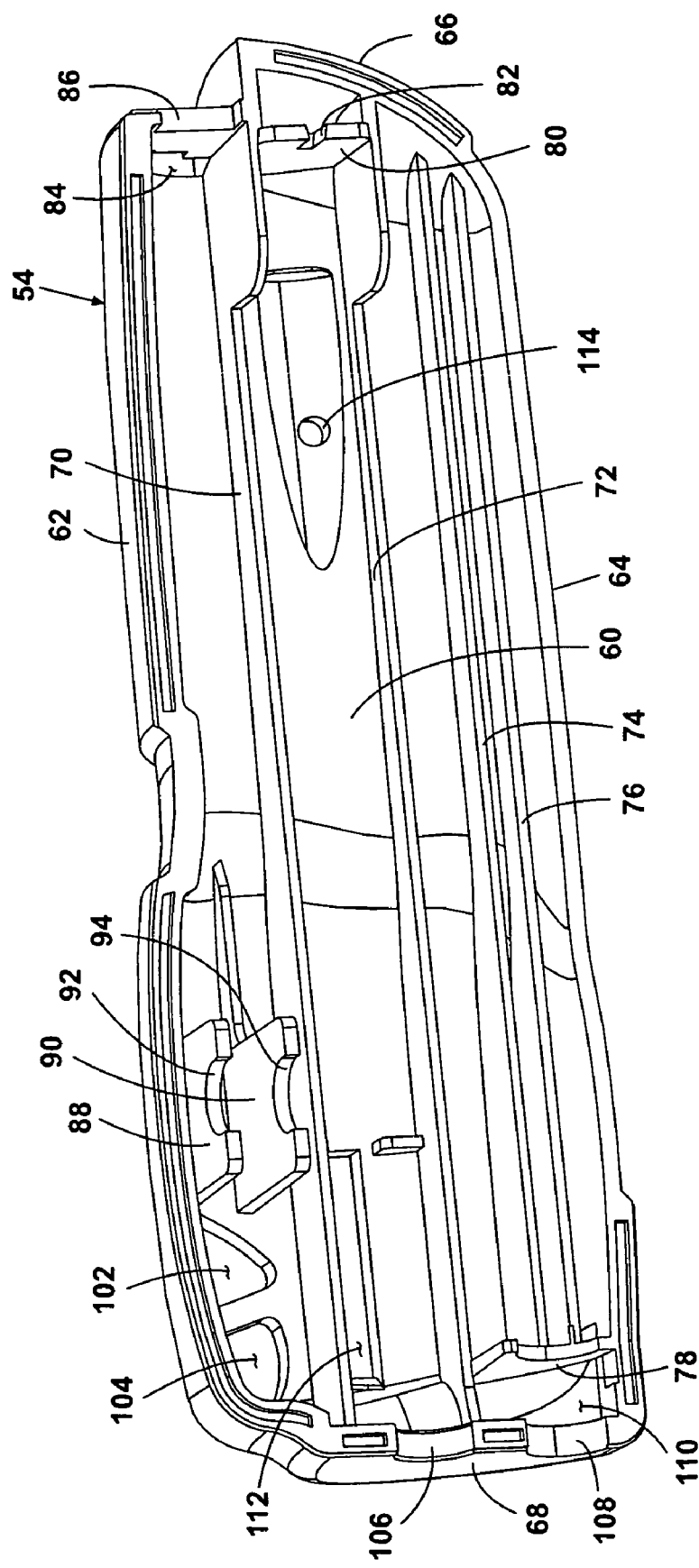
FIG. 6 is a perspective view of a left housing shell of the actuator assembly.
Figure 7:
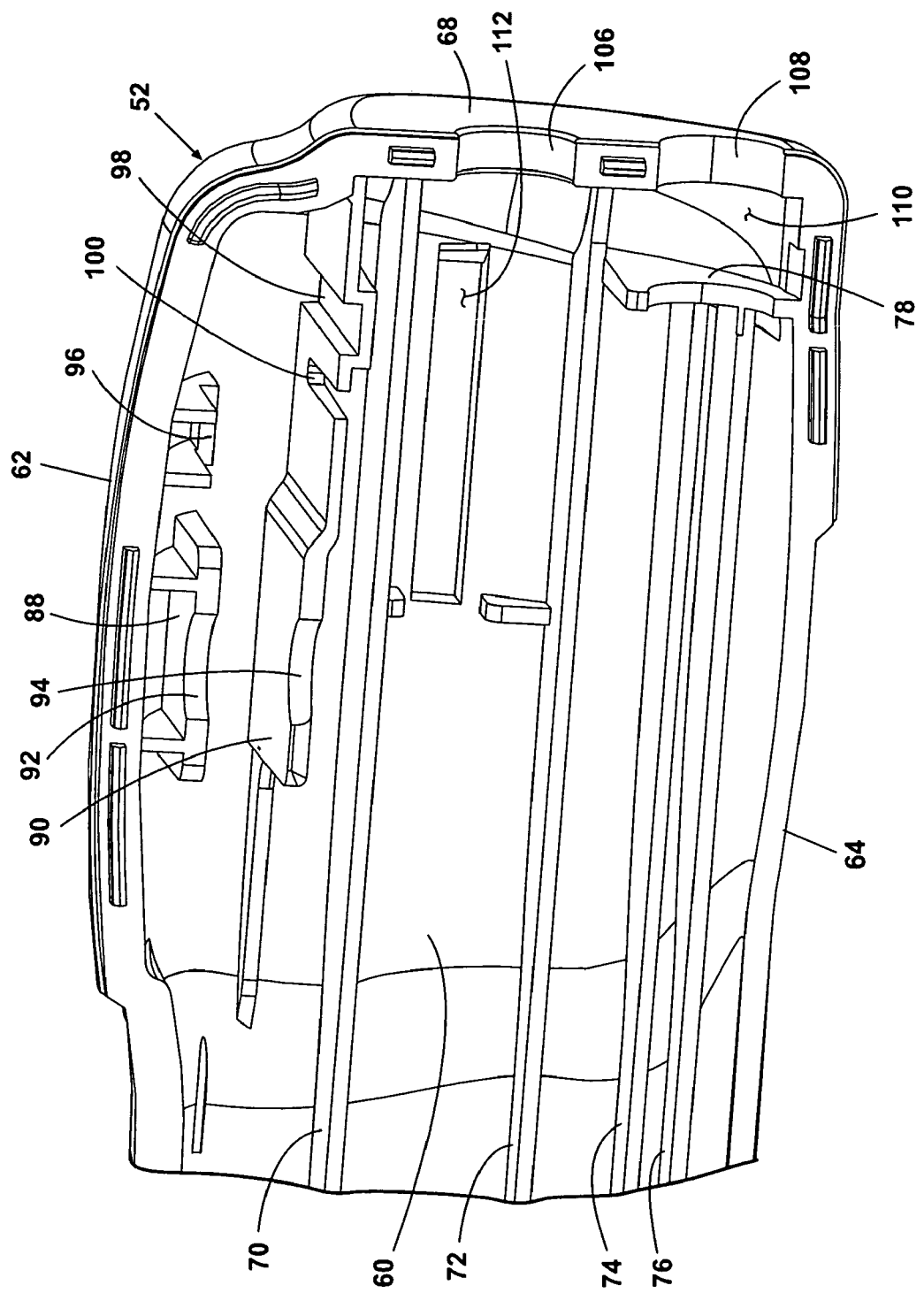
FIG. 7 is a partial perspective view of a right housing shell of the actuator assembly.

Referring to FIGS. 6-7, the left housing shell 54, which is an irregularly-shaped, elongated body, comprises an elongated sidewall 60 joined to a top wall 62, a bottom wall 64, a proximal wall 66, and a distal wall 68. The walls are contoured, and configured with openings, bosses, rails, and the like, for operational support of the elements comprising the biopsy device 10. The right housing shell 52, shown partially in FIG. 7, is generally a mirror image of the left housing shell 54, and has many of the same structural elements of the left housing shell 54 arranged for cooperative registry of the structural elements in both shells 52, 54 to provide support and movement functionality to the assembled outer housing 40. Accordingly, the term "chamber" as used in the description of the left housing shell 54, unless otherwise noted, is used with the understanding that any such chamber is formed between structural elements of the assembled housing shells 52, 54.

The left housing shell 54 comprises an upper guide rail 70 and a lower guide rail 72 in parallel, spaced-apart juxtaposition extending inwardly from the sidewall 60 between the proximal and distal walls 66, 68. The left housing shell 54 further comprises an upper alignment rail 74 and a lower alignment rail 76, also in parallel, spaced-apart juxtaposition, located below the lower guide rail 72 and extending inwardly from the sidewall 60 between the proximal wall 66 and a retaining wall 78. A spring guide retaining wall 80 extends between the guide rails 70, 72 near the proximal end of the left housing shell 54 and includes a mounting aperture 82. The left housing shell 54 further comprises a cocking element aperture 84 and a rectangular opening 86 in the proximal wall 66. When the housing shells 52, 54 are assembled, the rectangular openings 86 register to form a single center cocking element aperture (not shown); thus, in total, the outer housing 40 comprises three cocking element apertures.

The left housing shell 54 further comprises an upper lever support wall 88 and a lower lever support wall 90 in parallel, spaced-apart juxtaposition extending inwardly from the sidewall 60 above the upper guide rail 70. The lever support walls 88, 90 respectively comprise pivot apertures 92, 94. Referring to FIG. 7, the right housing shell 52 further comprises a first retaining slot 96 formed on the top wall 62 and a second retaining slot 98 formed on the lower lever support wall 90. The lower lever support wall 90 further comprises a spring hook slot 100. As shown in FIG. 6, the left housing shell 54 does not comprise the retaining slots 96, 98 or the hook slot 100, but does comprise a pair of button apertures 102, 104 formed in the sidewall 60 near the distal wall 68.

The left housing shell 54 further comprises an upper aperture 106 and a lower aperture 108 formed in the distal wall 68. The lower aperture 108 opens into a chamber 110 extending from the distal wall 68 to the retaining wall 78. An elongated indicator window 112 is formed in the sidewall 60 between the guide rails 70, 72. A circular indicator window 114 is formed in the sidewall 60 between the guide rails 70, 72, proximally of the elongated indicator window 112.

Referring to FIG. 3, the cocking/operation assembly 42 comprises a cocking element 116, a cocking element spring 118, a cannula carriage 120 which carries the cannula 20, a stylet carriage 122 which carries the stylet 22, a cannula spring 124, a stylet spring 126, and a spring guide 128. The cocking element 116 is slidably mounted to the outer housing 40 for movement between a first position (FIG. 12A) and a second position (FIG. 12C), which defines a single arming stroke of the biopsy device 10. As illustrated herein, in the first position, the cocking element 116 is retracted into the outer housing 40 and in the second position; the cocking element 116 is extended in a proximal direction from the outer housing 40. The cannula and stylet carriages 120, 122 are sequentially engaged by the cocking element 116 to draw the cannula 20 and stylet 22 back to an armed position (FIG. 12F). The spring guide 128 mounts the springs 124, 126, which act to bias the cannula and stylet carriages 120, 122 to a fired position (FIG. 12A). The cannula carriage 120 can be laterally offset from the operational axis X in the first lateral direction A and the stylet carriage 122 can be laterally offset from the operational axis X in the second lateral direction B.

Figure 8A:
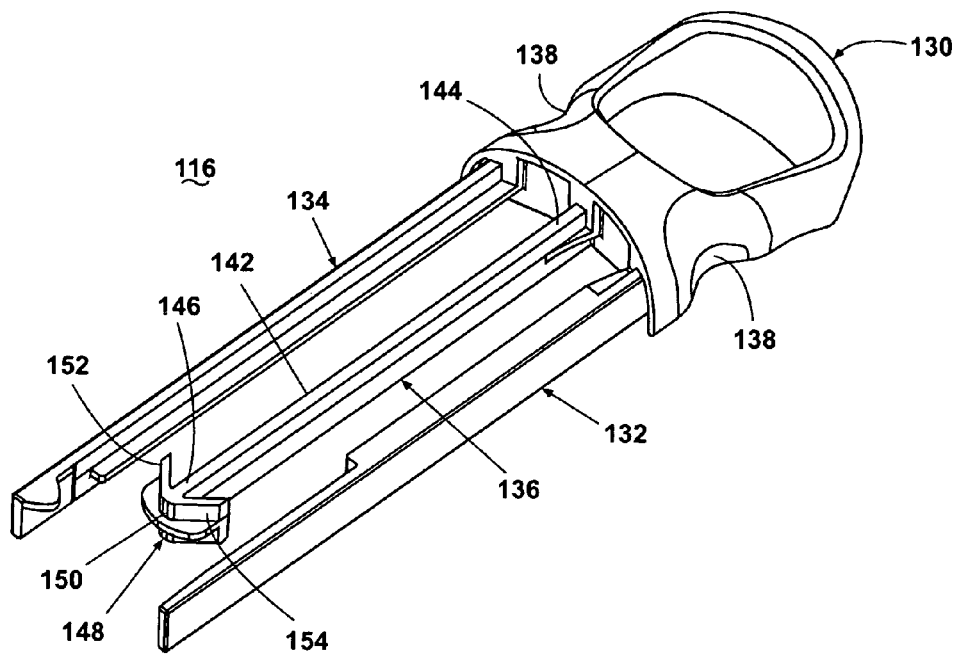
FIG. 8A is a top perspective view of a cocking element of the cocking/operation assembly of FIG. 3.
Figure 8B:
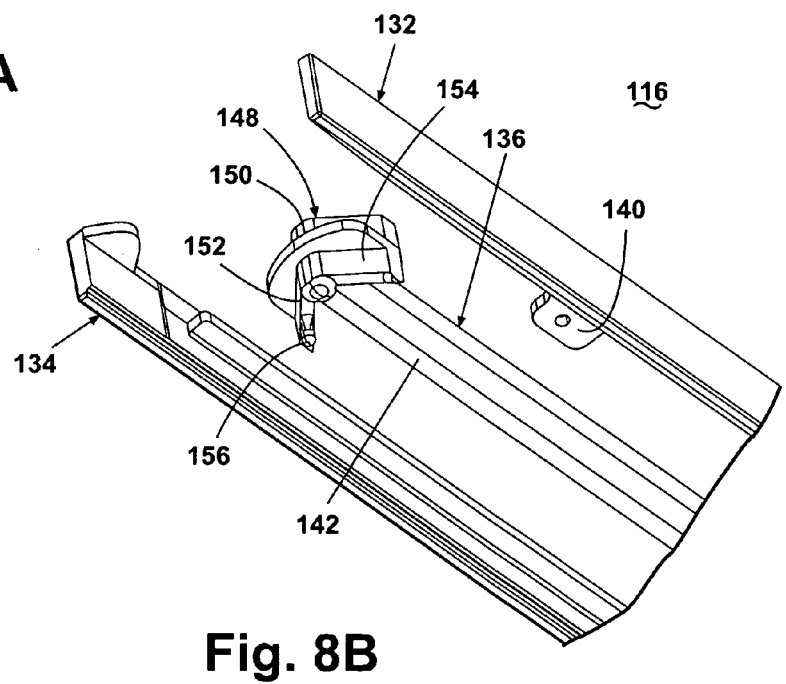
FIG. 8B is a bottom perspective view of the cocking element of FIG. 8A.

Referring to FIGS. 8A-8B, the cocking element 116 comprises a pull 130 having two distally extending, laterally spaced alignment members 132, 134 and a central cocking member 136 extending distally from the pull 130 between the alignment members 132, 134. The pull 130 is provided on the exterior of the outer housing 40, with the alignment members 132, 134 extending through the cocking element apertures 84 to guide the movement of the cocking element 116 relative to the outer housing, and the flexible cocking member 136 extending through the aperture created by the rectangular openings 86. The pull 130 is configured to be grasped by the user to draw the cocking element 116 to the second position in a proximal direction. As such, the pull 130 can be contoured to provide a comfortable grip to the user. As illustrated herein, the pull 130 is ring-shaped and includes two contoured portions 138 against which the user can brace a finger or thumb. The right alignment member 132 includes a spring mounting tab 140. The cocking element spring 118 is attached between the spring mounting tab 140 and the spring hook slot 100 formed on the right housing shell 52, and functions to bias the cocking element 116 to the first position, i.e. toward the distal wall 68.

The cocking member 136 includes an elongated flexible or resilient shaft 142 that extends along the operational axis X of the biopsy device 10 and comprises a proximal end 144 connected to the pull 130 and a distal free end 146 that includes a catch 148. The shaft 142 can be configured to be flexible or resilient such that the catch 148 can be displaced or deflected laterally from the operational axis X in the direction A or B, shown in FIGS. 13B and 13E. As illustrated herein, the catch 148 comprises an arrow-shaped lug 150 formed by two angled arms 152, 154. A guide pin 156 extends downwardly from the lower surface of the left angled arm 154.

Figure 9A:
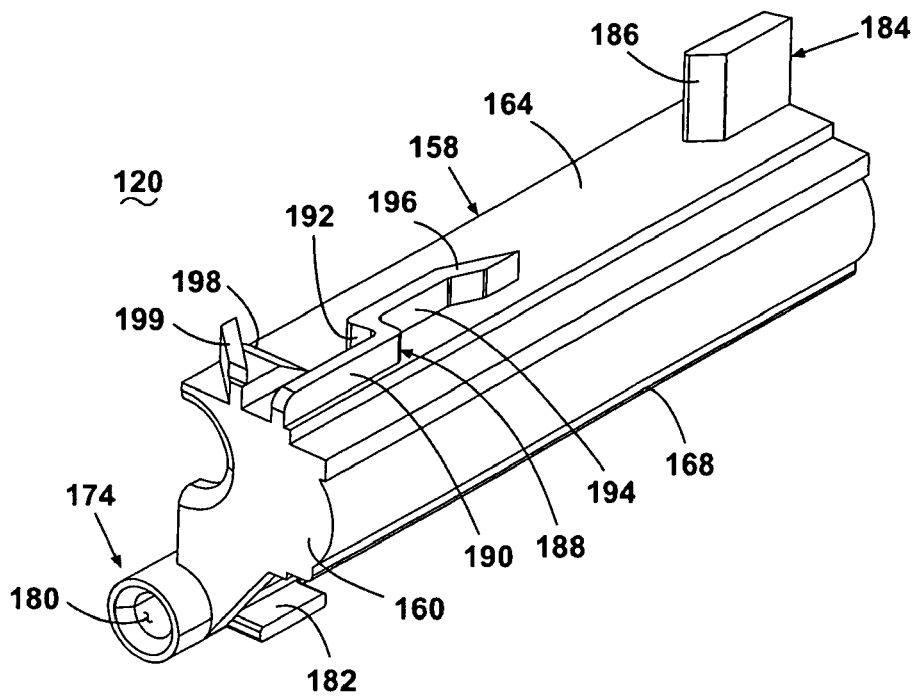
FIG. 9A is a top perspective view of a cannula carriage of the cocking/operation assembly of FIG. 3.
Figure 9B:
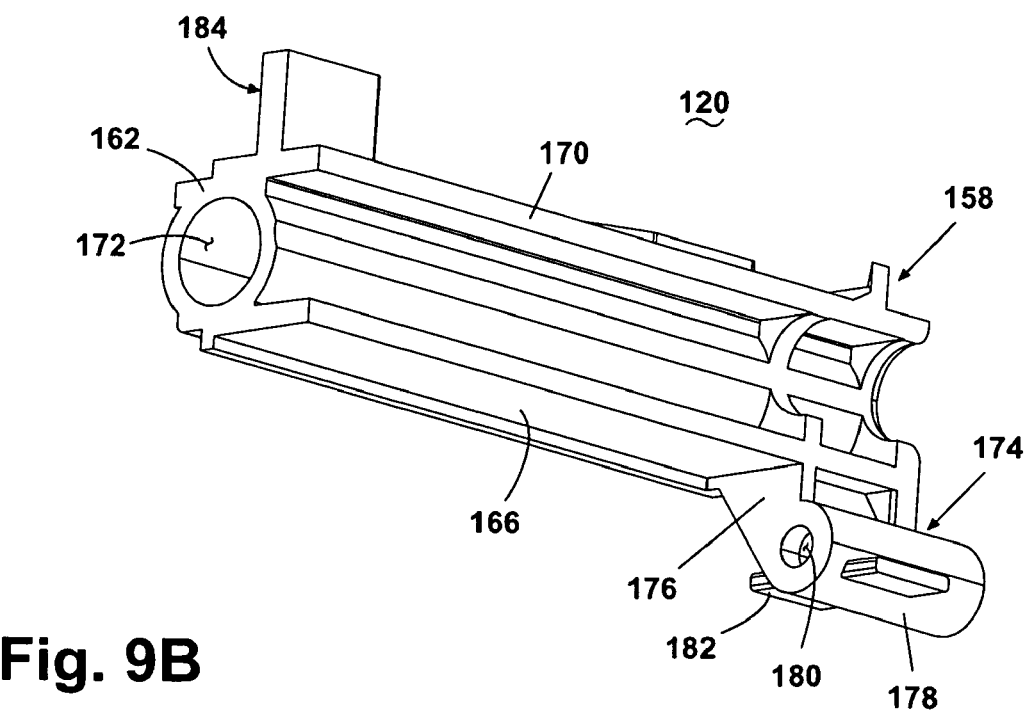
FIG. 9B is a bottom perspective view of the cannula carriage of FIG. 9A.

Referring to FIGS. 9A-9B, the cannula carriage 120 comprises an irregularly-shaped body 158 having a distal face 160, a proximal face 162, an upper surface 164, a lower surface 166, a right side surface 168, and a left side surface 170. A spring chamber 172 that is open at the proximal face 162 extends into the body 158. A cannula support portion 174 extends from the lower surface 166 and includes an angled brace 176 connecting a barrel portion 178 to the body 158. The barrel portion 178 defines an open-ended cylindrical chamber 180 in which a proximal end of the cannula 20 is received. At least one alignment tab 182 projects from the barrel portion 178 and is received between the alignment rails 74, 76 on the left housing shell 54.

The cannula carriage 120 further comprises a strike in the form of a lug 184 projecting from the upper surface 164 that is adapted to be engaged by the catch 148 on the cocking element 116. The lug 184 is offset from the operational axis X in a first lateral direction A (FIG. 5) and includes an angled distal face 186. A stop 188 also projects from the upper surface 164 and is located distally of the lug 184. The stop 188 can include a blocking wall 190 and a retaining wall 192 formed in a general L-shape, with the retaining wall 192 oriented transversely to the operational axis X. An alignment wall 194 extends proximally from the retaining wall 192 and includes an angled portion 196. A ramp 198 is formed on the upper surface 164, also distally of the lug 184, and is further laterally offset to and slightly distal of the retaining wall 192. A rib 199 projects from the ramp 198 and is angled toward the stop 188.

Figure 10A:
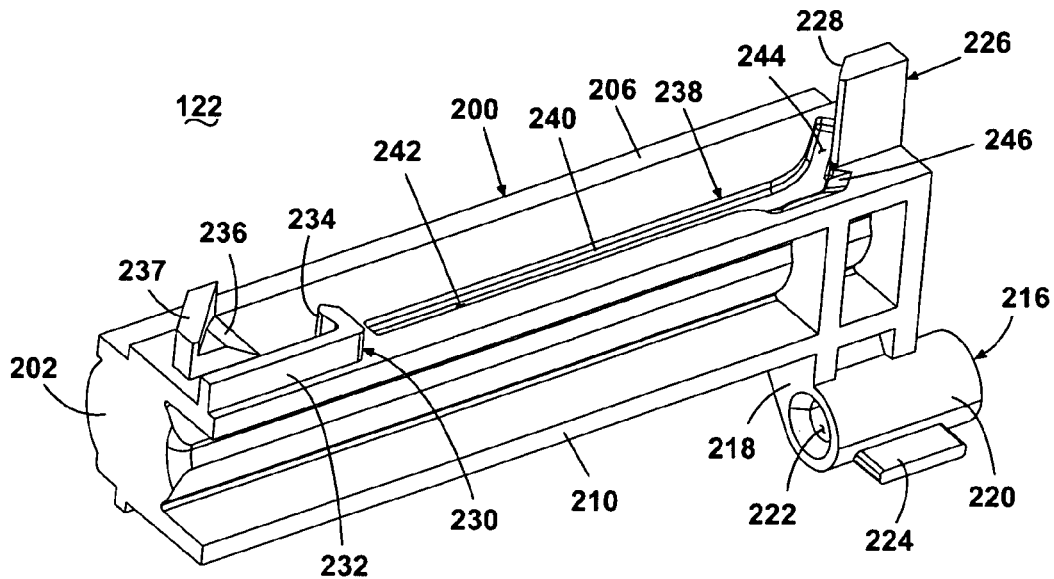
FIG. 10A is a top perspective view of a stylet carriage of the cocking/operation assembly of FIG. 3.
Figure 10B:
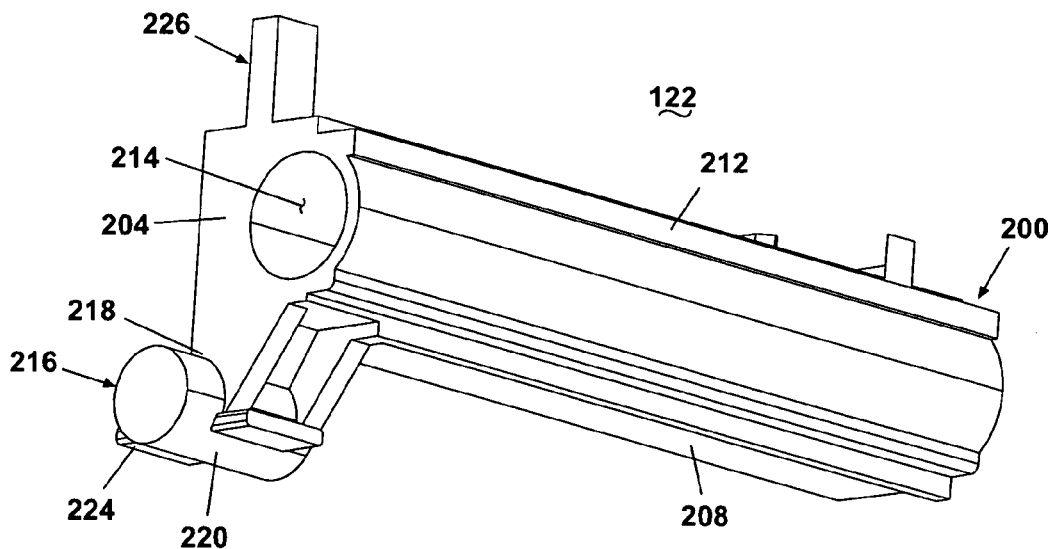
FIG. 10B is a bottom perspective view of the stylet carriage of FIG. 10A.

Referring to FIGS. 10A-10B, the stylet carriage 122 comprises an irregularly-shaped body 200 having a distal face 202, a proximal face 204, an upper surface 206, a lower surface 208, a right side surface 210, and a left side surface 212. A spring chamber 214 that is open at the proximal face 204 extends into the body 200. A stylet support portion 212 extends from the lower surface 208 and includes an angled brace 218 connecting a barrel portion 220 to the body 200. The barrel portion 220 defines an open-ended cylindrical chamber 222 in which a proximal end of the stylet 22 is received. At least one alignment tab 224 projects from the barrel portion 220 and is received between the alignment rails 74, 76 on the right housing shell 52. The stylet support portion 216 is coaxially aligned with the cannula support portion 174 such that the stylet 22 can pass through the lumen 26 cannula 20, thus passing through the barrel portion 178 of the cannula support portion 174.

The stylet carriage 122 further comprises a strike in the form of a lug 226 projecting from the upper surface 206 that is adapted to be engaged by the catch 148 on the cocking element 116. The lug 226 is offset from the operational axis X in a second lateral direction B that is opposite the first lateral direction A (FIG. 5) and includes an angled distal face 228. When the biopsy device 10 is assembled and the carriages 120, 122 are in the fired position, the angled distal face 228 on the stylet lug 226 is proximally spaced from the angled distal face 186 on the cannula lug 184. A stop 230 also projects from the upper surface 206 and is located distally of the lug 226. The stop 230 can include a blocking wall 232 and a retaining wall 234 formed in a general L-shape, with the retaining wall 234 oriented transversely to the operational axis X. A ramp 236 is formed on the upper surface 164, also distally of the lug 184, and is further laterally offset to and slightly distal of the retaining wall 192. A rib 237 projects from the ramp 236 and is angled toward the stop 230.

The biopsy device 10 can further include an alignment device 238 that is configured to maintain the resilient shaft 142 of the cocking element 116 in alignment with the operational axis X. The alignment device 238 can comprise a track 240 for guiding the movement of the catch 148 during the arming strokes. As illustrated herein, the track 240 is formed as an elongated recess in the upper surface 206 of the stylet carriage 122. The guide pin 156 formed on the catch 148 will ride along the track 240 during an arming stroke to ensure that the resilient shaft 142 travels along the operational axis X. The track 240 can include a linear section 242 that is generally parallel to the operational axis X and an angled section 244 that is continuous with the linear section 242 and that is oriented at an angle with respect to the operational axis X. The angled section 244 is configured to guide the catch 148 towards the stylet lug 226. The track 240 can further include an exit ramp 246 formed in the linear section 242 just distal to the angled section 244. The exit ramp permits the guide pin 156 to leave the track 240 when the catch 148 engages the cannula lug 184 during a first arming stroke, and thus not follow the track 240 to the angled section 244.

Referring to FIG. 3, the spring guide 128 comprises a plate-like base 248 with two laterally spaced, juxtaposed rods 250 extend orthogonally from the distal surface of the base 248. A tab (not shown) extends orthogonally from the proximal surface of the base 248 and is received in the mounting aperture 82 of the spring guide retaining wall 80 (FIG. 6) to mount the spring guide 128 within the outer housing 40. When assembled, the rods 250 extend through the spring chambers 172, 214 on one of the cannula and stylet carriages 120, 122, with the cannula spring 124 received on the right rod 250 between the base 248 and the distal wall 160 of the cannula holder 120 and the stylet spring 126 received on the left rod 250 between the base 250 and the distal wall 202 of the stylet carriage 122.

Figure 11:
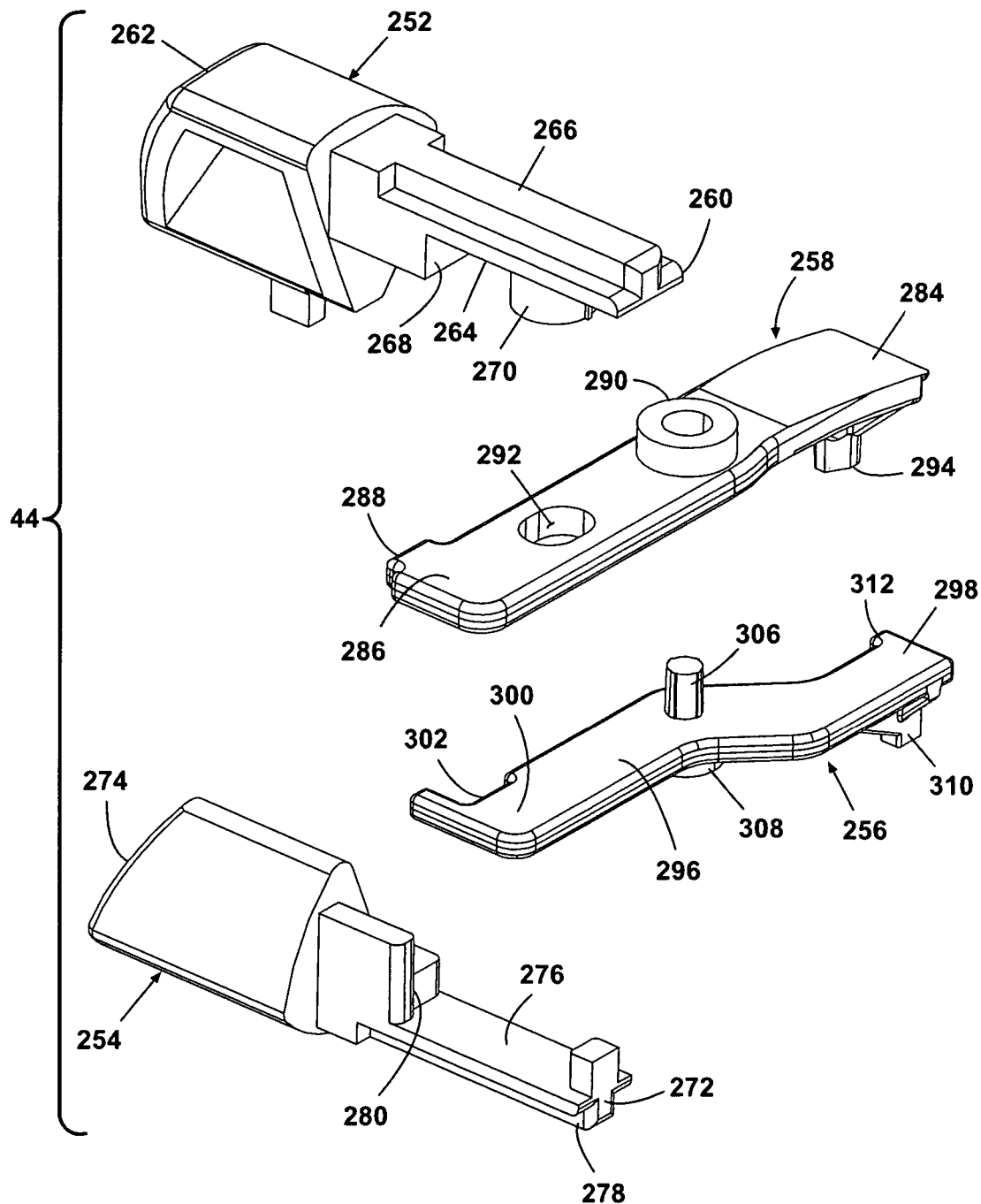
FIG. 11 is an exploded view of an actuator assembly of the biopsy device.

Referring to FIG. 11, the actuator assembly 44 comprises a first button 252, a second button 254, a cannula retainer 256 and a stylet retainer 258. The first button 252 functions to fire the stylet 22 alone. The second button 254 functions to sequentially fire the stylet 22 and the cannula 20 in rapid succession, or, if the stylet 22 has already been fired via the first button 252, the fire the cannula 20 alone. The cannula retainer 256 is operably coupled between the second button 254 and the cannula carriage 120. The cannula retainer 256 engages the stop 188 formed on the cannula carriage 120 to releasably retain the cannula carriage 120 in the armed position. The cannula retainer 256 is configured to be moved into engagement with the stop 188 during the first arming stroke of the biopsy device 10. The stylet retainer 258 is operably coupled between the first button 252 and the stylet carriage 122. The stylet retainer 258 engages the stop 230 formed on the stylet carriage 122 to releasably retain the stylet carriage 122 in the armed position. The stylet retainer 258 is configured to be moved into engagement with the stop 230 during the second arming stroke of the biopsy device 10.

In the illustrated embodiment, the first button 252 comprises a shaft 260 and a button head 262 connected to an end of the shaft 260. The shaft 260 includes a rectangular recessed area 264 formed on a lower surface thereof in which the stylet retainer 258 is received, and a tongue 266 formed on the upper surface thereof which is slidably received in the first retaining slot 96 on the right housing shell 52 (FIG. 7). The recessed area 264 includes a bearing wall 268 that is sized to selectively bear against the stylet retainer 258. A circular boss 270 is formed in the recessed area 264 and projects downwardly from the shaft 260. The second button 254 comprises a shaft 272 and a button head 274 connected to an end of the shaft 272. The shaft 272 includes a rectangular recessed area 276 formed on an upper surface thereof in which both the cannula and stylet retainers 256, 258 are received, and a tongue 278 formed on the lower surface thereof which is slidably received in the second retaining slot 98 on the right housing shell 52 (FIG. 7). The recessed area 276 includes a bearing wall 280 that is sized to selectively bear against both the cannula and stylet retainers 256, 258.

The stylet retainer 258 comprises a lever 282 having a proximal end 284 and a distal end 286. A projection 288 extends laterally from a side of the lever 282 near the distal end 286. A hollow pivot boss 290 extends orthogonally upward from approximately the midpoint of the lever 282 and is rotatably received in the upper pivot aperture 92 on the right housing shell (FIG. 7). A button opening 292 is formed in the lever 282 between the projection 288 and the pivot boss 290 and receives the circular boss 270 on the first button 252. A catch 294 depends orthogonally downward from the lever 282 near the proximal end 284.

The cannula retainer 256 comprises a lever 296 having a proximal end 298 and a distal end 300. A recess 302 is formed a side of the lever 296 near the distal end 300 and receives the bearing wall 280 of the second button 254. A pivot pin 306 extends orthogonally upward from approximately the midpoint of the lever 296 and is received in the hollow pivot boss 290 on the stylet retainer 258 such that both retainers 256, 258 pivot about a common axis. A pivot boss 308 extends orthogonally downward from the lever 296 and is generally aligned with the pivot pin 306. The pivot boss 308 is rotatably received in the lower pivot aperture 94 on the right housing shell (FIG. 7). A catch 310 depends orthogonally downward from the lever 296 near the proximal end 298. A projection 312 extends laterally from a side of the lever 296 near the proximal end 298.

Referring to FIG. 3, the sample size control assembly 46 comprises an adjusting member 320, an adjuster wheel 322, a gear 324 coupling the adjuster member 320 and the adjusting wheel 322, and a throw stop 326 coupled to the adjuster member 320. The adjuster wheel 322 is rotated to select the size of the biopsy sample the biopsy device 10 will collect. The rotation of the adjuster wheel 322 is transmitted to the adjusting member 320 by the gear 324. The rotation of the adjusting member 320 is in turn translated to linear movement of the throw stop 326 relative to the outer housing 40. When fired, the cannula and stylet carriages 120, 122 will strike the throw stop 326. Therefore, the location of the throw stop 326 relative to the outer housing 40 will determine the distance the carriages 120, 122 can travel and consequently can determine the fired position of the carriages 120, 122. The throw stop 326 further includes a pair of outer tips 328 that are visible in the indicator windows 112 and can indicate the position of the throw stop 326 relative to the outer housing 40, which in turn can indicate the specimen size the biopsy device is set to collect since the position of the throw stop 326 determines the distance the cannula and stylet carriages 120, 122 can travel relative to the outer housing 40.

A damper 330 can optionally be provided between the cannula and stylet carriages 120, 122 and the throw stop 326 to provide noise dampening, vibration dampening, and/or shock absorption. As illustrated herein, the damper 330 comprises a relatively flat member located on the proximal face of the throw stop 326, in which case the cannula and stylet carriages 120, 122 will strike the proximal face of the damper 330 when fired. The damper 330 can be attached to the throw stop 326 using a pressure sensitive adhesive. The damper 330 can be fabricated from a material that provides noise dampening, vibration dampening, and/or shock absorption when contacted by the stylet carriage 122 and the cannula carriage 120, such as a polyurethane foam. The damper 330 can be configured to dampen the noise associated with firing the biopsy device 10. Optionally, the damper 330 can limit the noise to a level below that which triggers the acoustic startle reflex (also known as the acoustic startle response, both abbreviated as "ASR"), which is a reflex pattern or response a sudden unexpected stimulus, such as a loud noise, in the average human or in the majority of humans. Optionally, the damper 330 can limit the noise to under 115 decibels.

An exemplary description of the operation of the biopsy device 10 will now be described with reference to FIGS. 12A-H, 13A-I, and 14A-I. In the Figures, elements of the biopsy device 10 particularly the housing shells 52, 54, will be either removed or illustrated in phantom to facilitate a complete understanding of the operation of the biopsy device 10. The operation of the biopsy device 10 generally comprises the steps of: (i) cocking or arming the biopsy device 10; (ii) selecting the specimen size to be collected; (iii) firing the biopsy device 10 to collect a specimen; and (iv) retrieving the specimen from the biopsy device. It will be apparent to one of ordinary skill that the operation procedure can proceed in any logical order and is not limited to the sequence presented below. The following description is for illustrative purposes only and is not intended to limit the invention in any manner.

Referring to FIGS. 12A, 13A and 14A, the biopsy device 10 is initially in an uncocked or fired condition, and is typically cocked or armed prior to introducing the cannula assembly 12 into the tissue mass 16 (FIG. 1). In the uncocked condition, the cocking element 116 is urged distally to the first position by influence of the cocking element spring 118 and the carriages 120, 122 are urged distally against the throw stop 326 by their respective springs 124, 126.

As illustrated in FIGS. 12B, 13B and 14B, the cocking element 116 is pulled rearwardly or proximally a first time. As the guide pin 157 rides along the linear section 242 of the track 240, the left angled arm 154 on the catch 148 will contact the angled distal face 186 on the cannula lug 184 and deflect the cocking member 136 from the operational axis X in the first lateral direction A. This substantially coincides with the guide pin 156 reaching the end of the linear section 242, and the deflection of the cocking member 136 causes the guide pin 156 to ride up the exit ramp 246 and out of the track 240. The catch 148 thus clears the stylet lug 226 during the first arming stroke.

As illustrated in FIGS. 12C, 13C and 14C, under continued rearward pulling of cocking element 116 to the second position, the cannula carriage 120 moves rearwardly relative to the cannula retainer 256. As the cannula carriage 120 moves, the catch 310 will strike the angled section 196 of the alignment wall 194, which helps the catch 310 align with the ramp 198. The catch 310 on the cannula retainer 256 will ride up the ramp 198 and contact the rib 199, which forces the catch 310 toward the stop 188. The catch 310 will come to rest against the retaining wall 192 of the stop 188, thereby retaining the cannula carriage 120, and consequently the cannula 20, in the armed position.

As illustrated in FIGS. 12D, 13D and 14D, the cocking element 116 returns to the first position from the second position under the influence of the cocking element spring 118. However, the cocking element 116 could be manually returned to the first position by the user. As the catch 148 leaves the cannula lug 184, the cocking member 136 will move back into alignment with the operational axis. When the cocking element 116 begins to pass over the stylet holder 122, the right angled arm 152 will strike the stylet lug 226 and be temporarily deflected until the catch 148 clears the stylet lug 226 and the guide pin 156 reenters the track 240 and slides distally along the linear section 242 until the cocking element 116 reaches the first position.

As illustrated in FIGS. 12E, 13E and 14E, the cocking element 116 is pulled rearwardly or proximally a second time. As the guide pin 157 rides along the linear section 242 of the track 240, the right angled arm 152 on the catch 148 will contact the angled distal face 228 on the stylet lug 226 and deflect the cocking member 136 from the operational axis X in the second lateral direction B. This coincides with the guide pin 156 reaching the end of the linear section 242 and entering the angled section 244.

As illustrated in FIGS. 12F, 13F and 14F, under continued rearward pulling of cocking element 116, the stylet carriage 122 moves rearwardly relative to the stylet retainer 258. The catch 294 on the stylet retainer 258 will ride up the ramp 236 and contact the rib 237, which forces the catch 294 toward the stop 230. The catch 294 will come to rest against the retaining wall 234 of the stop 230, thereby retaining the stylet carriage 122, and consequently the stylet 22, in the armed position. The biopsy device 10 is now fully armed. The cocking element 116 returns to the first position from the second position under the influence of the cocking element spring 118. In the armed position, the stylet carriage 122 is partially visible in the indicator window 114 (FIG. 6) to indicate to the user that the biopsy device 10 is fully armed.

The specimen size to be collected can optionally be selected using the sample size control assembly 46 after the biopsy device 10 is fully armed. Alternately, the specimen size to be collected can be selected at any time prior to the insertion of the cannula assembly 12 into the tissue mass 16. The specimen size may be selected after insertion, but this is not currently desired.

With the biopsy device 10 in the fully armed position, the cannula assembly 12 is inserted into the tissue mass 16 so that the penetration tip 34 is adjacent the lesion 18. The biopsy device is then fired or actuated for excision of a biopsy sample or specimen using the actuator assembly 44. The actuator assembly 44 can be operated in one of two ways to obtain a biopsy sample. Both procedures initially fire the stylet 22 into the lesion 18 by releasing the stylet carriage 122 and thereafter fire the cannula 20 over the stylet 22 by releasing the cannula carriage 120. The two firing procedures are illustrated in FIGS. 12G-12H, 13G-13I, and 14G-14I, in which the cocking element 116 is removed to more clearly show the firing procedures.

As illustrated in FIGS. 12G, 13G and 14G, the first procedure comprises a two-step actuating operation. The first button 252 is pressed inward, i.e. in the first lateral direction A, which causes the stylet retainer 258 to pivot about the axis defined by the pivot boss 290 by the movement of the circular boss 270 against the button opening 292. The pivoting movement of the stylet retainer 258 moves the catch 294 out of engagement with the stop 230, thereby releasing the stylet carriage 122 to move distally under influence of the stylet spring 126 until the distal face 202 strikes the throw stop 236, or the optional damper 330, and causing the stylet 22 to be fired into the lesion 18.

As illustrated in FIGS. 12H, 13H and 14H, after a period of time which is completely at the control and discretion of the user of the biopsy device 10, the second button 254 is pressed inward, i.e. in the first lateral direction A, which causes the cannula retainer 256 to pivot about the axis defined by the pivot pin 306. The pivoting movement of the cannula retainer 256 moves the catch 310 out of engagement with the stop 188, thereby releasing the cannula carriage 120 to move distally under influence of the cannula spring 124 until the distal face 160 strikes the throw stop 236, or the optional damper 330, and causing the cannula 20 to be fired into the lesion 18 over the stylet 22.

This procedure provides the user with the ability to reposition the biopsy device 10 if need be after the firing of the stylet 22. For example, the user may fire the stylet 22, confirm that the notch 36 is in the desired location within the tissue mass 16 by some imaging technique, such as ultrasound, and then fire the cannula 20 to sever the tissue sample from the tissue mass 16.

Figure 13I:
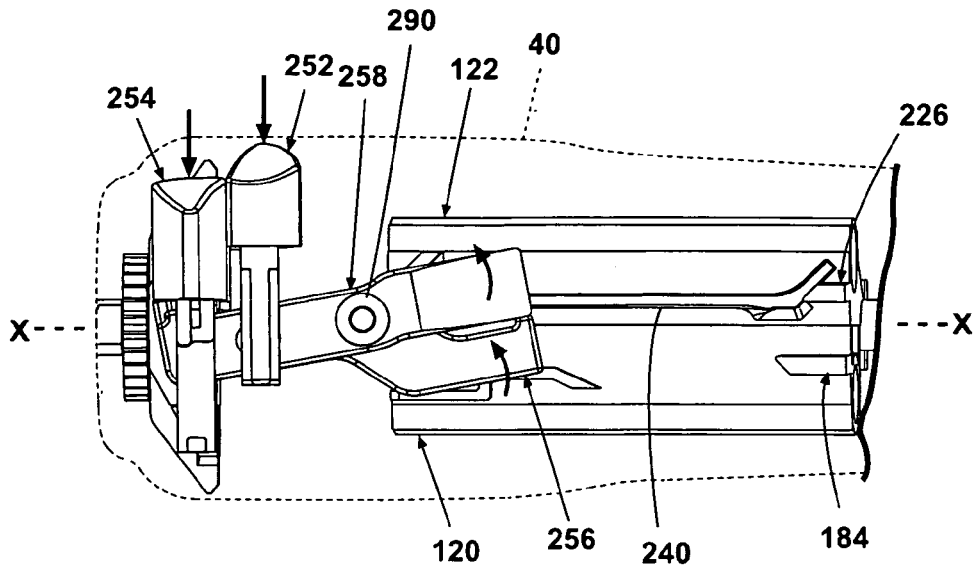
Figure 14I:
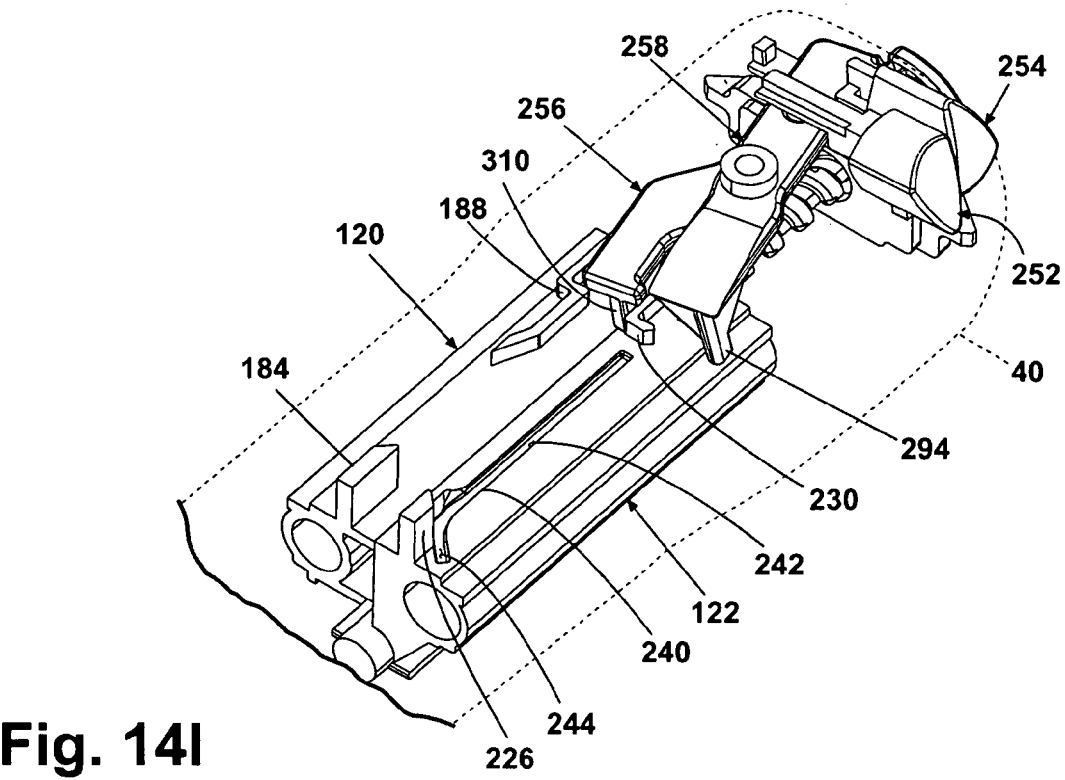

As illustrated in FIGS. 13I and 14I, the second procedure comprises a one-step actuating operation. Without having initially pressed the first button 252, the second button 254 is pressed inward, i.e. in the first lateral direction A. The bearing wall 280 will contact the projection 288 on the stylet retainer 258 first, which causes the stylet retainer 258 to pivot, initiating the sequence of events described above with respect to FIG. 12G which culminates with the firing of the stylet 22 into the lesion 18. Pressing the second button 245 farther inward causes the bearing wall 280 to contact the cannula retainer 256, which causes the cannula retainer 256 to pivot and initiate the sequence of evenings described above with respect to FIG. 12H which culminates with the firing of the cannula 20 in the lesion over the stylet 22. As the second button 254 is pressed inward, the first button 252 also moves inward per the rotation of the cannula retainer 256. Thus, a single action by the user, i.e. pressing the button 254, can automatically and sequentially actuate the stylet 22 and the cannula 20.

The second method provides the user with the ability to quickly sever the tissue specimen from the tissue mass 16 after the firing of the stylet 22. This method enhances the likelihood that the notch 36 will not move relative to the desired location in the tissue mass 16 before the severing of the tissue specimen by the cannula 20.

After either of the actuating operations, the biopsy device 10 is reset to its fired position. The cannula assembly 12 can then be withdrawn from the tissue mass 16 with a biopsy sample retained in the notch 26 of the stylet 22. Performing a first arming stroke will cause the cannula 20 to move proximally relative to the stylet 22 to expose the notch 26 and permit retrieval of the biopsy sample.

Referring to FIGS. 15-17C, certain features of a second embodiment of the biopsy device 10 are illustrated. The biopsy device 10 is substantially similar to that of the first embodiment, with the exception of the cocking element 116 and the spring guide 128. Referring to FIG. 15, the cocking element 116 of this embodiment is modified so that the left angled arm 154 of the catch 148 is longer than the right angled arm 152. This modification will affect the operation of the second embodiment as compared to the first embodiment of the biopsy device, as described above, during the cocking or arming step. During a first retraction of the cocking element 116, the left angled arm 154 is intended to catch the lug 184 on the cannula carriage 120. However, if the angled arm 154 misses the lug 184 or if instead the right angled arm 152 catches the lug 226 on the stylet carriage 120, the biopsy device 10 will not be properly armed. Increasing the length of the left angled arm 154 increases the likelihood of catching the lug 184 on the cannula carriage 120 during the first retraction of the cocking element 116, thus increasing the likelihood that the biopsy device 10 is properly armed during each use.

Referring to FIGS. 16A and 16B, the spring guide 128 of this embodiment is modified to include a plate-like middle rod 332 extending orthogonally from the distal surface of the base 248 in between the outer spaced rods 250. A delay arm 334 is movably mounted to the middle rod 332, and functions to delay movement of the cannula carriage 120 during firing. The delay arm 334 comprises an elongated body 336 with a projection 338 formed near its distal end and a pivot boss 340 formed near its proximal end and which fits into a hollow pivot boss 342 on the bottom side of the middle rod 332 to pivotally mount the delay arm 334 to the middle rod 332. When assembled, the middle rod extends between the carriages 120, 122 to separate them, and the projection 338, when the biopsy device 10 is armed, extends in front of the distal face 160 of the cannula carriage 120.

Referring to FIG. 17A-C, this modification will affect the operation of the second embodiment as compared to the first embodiment biopsy device, as described above, during the firing step, and essentially only when using the one-step actuating operation. During the one-step actuating operation, the release of the stylet carriage 122 and the release thereafter of the cannula carriage 120 is fully automatic, and can be difficult to time correctly. If the timing is too fast, only a small amount of tissue can prolapse into the stylet notch 36 before the cannula 20 is extended, resulting in an insufficiently small specimen. The delay arm 334 is designed to delay the movement of the cannula carriage 120 for a predetermined period of time while the stylet carriage 122 advances during firing, as shown in FIG. 17A. The addition of the delay arm 334 is a convenient way to correctly time the advancement of the cannula 20 over the stylet 22. After the release of the cannula carriage 120, described above with respect to FIGS. 13I and 14I, the cannula carriage 120 begins to move distally, but is delayed by the projection 338 in front of the distal face 160, as shown in FIG. 17B. Referring to FIG. 17C, the continued distal movement of the cannula carriage 120 causes the delay arm 334 to pivot about an axis defined by the pivot boss 340 to move the projection 338 out of the way and allow the cannula carriage 120 to complete its distal movement.

The biopsy device 10 described herein provides several distinct benefits to the user. The cannula and stylet carriages 120, 122 are selectively engaged by the flexible cocking member 136 to arm the cannula 20 and stylet 22. The alignment device 238 guides the lateral movement of the flexible cocking member 136 so that upon the first arming stroke, the cannula carriage 120 is armed and upon the second arming stroke, the stylet carriage 122 is armed. Because the biopsy device 10 is cocked using two separate arming strokes, the user has to apply only enough force to overcome one biasing spring 124, 126 at time. The two-step cocking method has the added benefit of exposing the notch 36 upon the first arming stroke so that a biopsy sample can be retrieved from the cannula assembly 12. The use of a sample size control assembly further allows the user to select the size of the biopsy sample to be collected.

While the invention has been specifically described in connection with certain specific embodiments thereof, it is to be understood that this is by way of illustration and not of limitation. Reasonable variation and modification are possible within the scope of the forgoing disclosure and drawings without departing from the spirit of the invention which is defined in the appended claims.

What is claimed is:

1. A biopsy device for the percutaneous removal of a specimen from a tissue mass, the biopsy device comprising:
    a housing defining an interior having an operational axis;
    a cannula carriage provided in the housing for reciprocal movement between an armed position and a fired position within the interior and having a cannula strike laterally offset from the operational axis in a first lateral direction;
    a stylet carriage provided in the housing for reciprocal movement between an armed position and a fired position within the interior and having a stylet strike laterally offset from the operational axis in a second lateral direction opposite the first lateral direction and proximal of the cannula strike when the cannula carriage and the stylet carriage are in the fired position; and
    a cocking element slidably mounted to the housing for movement between a first position and a second position to define an arming stroke, and having a catch integrally formed with a resilient shaft extending along the operational axis;
    wherein the catch, when the stylet and cannula carriages are in the fired positions, is configured to engage the cannula strike, upon a first arming stroke, to deflect the resilient shaft from the operational axis in the first lateral direction such that the catch clears the stylet strike and moves the cannula carriage to the armed position.

2. The biopsy device according to claim 1 wherein the catch is configured to engage the stylet strike, upon a second arming stroke, to deflect the resilient shaft from the operational axis in the second lateral direction to move the stylet carriage to the armed position when the cannula carriage is in the armed position.

3. The biopsy device according to claim 2, wherein the catch comprises an arrow-shaped lug having a first angled arm configured to engage the cannula strike during the first arming stroke and a second angled arm configured to engage the stylet strike during the second arming stroke.

4. The biopsy device according to claim 3 wherein the cannula strike comprises an angled distal face configured to engage the first angled arm during the first arming stroke to deflect the resilient shaft from the operational axis.

5. The biopsy device according to claim 4 wherein the stylet strike comprises an angled distal face that is proximal the distal face of the cannula strike when the cannula carriage is in the fired position and is configured to engage the second angled arm during the second arming stroke.

6. The biopsy device according to claim 2 and further comprising an alignment device configured to maintain the resilient shaft in alignment with the operational axis.

7. The biopsy device according to claim 6 wherein the alignment device comprises a track for guiding the movement of the catch during the first and second arming strokes.

8. The biopsy device according to claim 7 wherein the track is formed in the stylet carriage.

9. The biopsy device according to claim 7 wherein the catch comprises a pin configured to ride within the track.

10. The biopsy device according to claim 9 wherein the track is configured to guide the catch toward the stylet strike during the second arming stroke.

11. The biopsy device according to claim 1 further comprising: a stylet carried by the stylet carriage; and
    a cannula carried by the cannula carriage and defining a lumen for receiving the stylet.

12. The biopsy device according to claim 1 wherein the cannula carriage is laterally offset from the operational axis in the first lateral direction and the stylet carriage is laterally offset from the operational axis in the second lateral direction.

13. The biopsy device according to claim 1 wherein the cocking element further comprises a pull coupled to the resilient shaft opposite the catch and located on the exterior of the housing, wherein the pull is configured to be grasped by a user and pulled proximally to move the cocking element from the first position to the second position.

14. The biopsy device according to claim 13 wherein the housing comprises an enlarged bearing portion to allow a user's fingers to securely grip the housing while the pull is pulled proximally.

15. The biopsy device according to claim 2 further comprising an actuator operably coupled to the stylet carriage and the cannula carriage to sequentially move each of the stylet carriage and cannula carriage from the armed position to the fired position.

16. The biopsy device according to claim 15, wherein the actuator further comprises a stylet retainer configured to engage a stylet stop formed on the stylet carriage to releasably retain the stylet carriage in the armed position and a cannula retainer configured to engage a cannula stop formed on the cannula carriage to releasably retain the cannula carriage in the armed position.

17. The biopsy device according to claim 16 wherein the cannula retainer is configured to be moved into engagement with the cannula stop during the first arming stroke and the stylet retainer is configured to be moved into engagement with the stylet stop during the second arming stroke.

18. The biopsy device according to claim 17 wherein the retainers comprise levers which are pivotably mounted within the housing.

19. The biopsy device according to claim 17 wherein the actuator further comprises:
    a first button mounted to the housing and operably coupled to the stylet retainer; and
    a second button mounted to the housing and operably coupled to both the stylet retainer and the cannula retainer;
    wherein the first button is configured to release the stylet retainer from the stylet stop when pressed and the second button is configured to release the cannula retainer from the cannula stop when pressed.

20. The biopsy device according to claim 19 wherein the second button is configured to release the stylet retainer from the stylet stop prior to releasing the cannula retainer from the cannula stop when the second button is pressed before the first button is pressed.

21. The biopsy device according to claim 1 further comprising a delay arm in the housing configured to delay the movement of the cannula carriage when moving the cannula carriage from the armed position to the fired position.

* * * * *